US012636160B2

(12) United States Patent     (10) Patent No.:   US 12,636,160 B2
Dacosta et al.     (45) Date of Patent:     May 26, 2026

(54) ORTHOPEDIC IMPLANTS, INSTRUMENT SYSTEMS AND METHODS OF USE

(71) Applicant: Paragon 28, Inc., Englewood, CO (US)

(72) Inventors: Albert Dacosta, Lone Tree, CO (US); Laura Zagrocki Brinker, Lone Tree, CO (US); Joseph Dogué, Aurora, CO (US); Benjamin Majors, Englewood, CO (US); Tristan Collette, Denver, CO (US); Richard David Hunt, Reno, NV (US); Spanky Raymond, Uniontown, OH (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 18/926,412

(22) Filed: Oct. 25, 2024

(65) Prior Publication Data

US 2025/0041070 A1     Feb. 6, 2025

Related U.S. Application Data

(63) Continuation of application No. PCT/US2023/066347, filed on Apr. 28, 2023.
(Continued)

(51) Int. Cl.
    *A61B 17/58*     (2006.01)
    *A61F 2/42*     (2006.01)
    (Continued)

(52) U.S. Cl.
    CPC ........ *A61F 2/4225* (2013.01); *A61B 17/8863* (2013.01); *A61F 2002/30535* (2013.01)

(58) Field of Classification Search
    None
    See application file for complete search history.

(56) References Cited

U.S. PATENT DOCUMENTS

| | | | |
|---|---|---|---|
| 11,395,686 B2 * | 7/2022 | Saw ................... | A61B 17/8095 |
| 12,402,915 B2 * | 9/2025 | Hollis ................ | A61B 17/7283 |

(Continued)

FOREIGN PATENT DOCUMENTS

| | | |
|---|---|---|
| EP | 1356778 | 10/2003 |
| EP | 3202348 | 8/2017 |

(Continued)

OTHER PUBLICATIONS

International Search Report and Written Opinion of the International Searching Authority for PCT/US2023/066347 dated Nov. 20, 2023, 8 pages.

(Continued)

*Primary Examiner* — Jan Christopher L Merene
(74) *Attorney, Agent, or Firm* — Heslin Rothenberg Farley & Mesiti P.C.; Jacquelyn A. Graff, Esq.

(57) ABSTRACT

An orthopedic implant includes an upper portion, a central portion having a greater lateral dimension than that of the upper portion, and a lower portion having a greater lateral dimension than the central portion. The upper portion, the central portion and the lower portion each may have at least one fixation aperture. Further, the upper portion, the central portion and the lower portion may each be non-linear and/or curved relative to at least one plane. An instrument having a body that includes a housing. The body includes a platform, at least one retention mechanism for holding the implant on the platform, an adjustment mechanism to adjust the height of the platform relative to the top surface of the housing, and a lid coupled with the housing with the top surface of the housing and the lid defining a slot configured to receive a cutting instrument.

12 Claims, 24 Drawing Sheets

Related U.S. Application Data

(60) Provisional application No. 63/366,184, filed on Jun. 10, 2022, provisional application No. 63/363,724, filed on Apr. 28, 2022.

(51) Int. Cl.
| | |
|---|---|
| *A61B 17/88* | (2006.01) |
| *A61F 2/30* | (2006.01) |

(56) References Cited

U.S. PATENT DOCUMENTS

| | | | | |
|---|---|---|---|---|
| 2002/0082604 | A1* | 6/2002 | Abdelgany | A61F 2/4644 |
| | | | | 623/16.11 |
| 2003/0135212 | A1* | 7/2003 | Y. Chow | A61B 17/8085 |
| | | | | 606/64 |
| 2005/0085818 | A1* | 4/2005 | Huebner | A61B 17/1728 |
| | | | | 606/291 |
| 2007/0233106 | A1* | 10/2007 | Horan | A61B 17/8061 |
| | | | | 606/282 |
| 2010/0016858 | A1* | 1/2010 | Michel | A61B 17/8061 |
| | | | | 606/70 |
| 2010/0030276 | A1* | 2/2010 | Huebner | A61B 17/8061 |
| | | | | 606/280 |
| 2013/0096680 | A1* | 4/2013 | Ribeiro | A61F 2/4644 |
| | | | | 606/88 |
| 2014/0039498 | A1* | 2/2014 | Chatain | A61B 17/8095 |
| | | | | 606/280 |
| 2016/0128745 | A1 | 5/2016 | Sidebotham et al. | |
| 2016/0310184 | A1* | 10/2016 | Kazanovicz | A61B 17/1739 |
| 2016/0338748 | A1 | 11/2016 | Champagne et al. | |
| 2017/0215931 | A1 | 8/2017 | Cremer et al. | |
| 2019/0008569 | A1* | 1/2019 | Wahl | A61B 17/8095 |
| 2023/0320858 | A1* | 10/2023 | Aksu | A61B 17/152 |
| | | | | 606/280 |
| 2024/0197498 | A1* | 6/2024 | Graul | A61F 2/30942 |
| 2025/0325312 | A1* | 10/2025 | Laird, Jr. | A61B 17/0401 |

FOREIGN PATENT DOCUMENTS

| | | |
|---|---|---|
| KR | 20160145864 | 12/2016 |
| WO | 2021215904 | 10/2021 |

OTHER PUBLICATIONS

International Preliminary Report on Patentability for International Application No. PCT/US2023/066347 dated Oct. 29, 2024, 5 pages.
Communication Pursuant to Rule 164(1) EPC from European Patent Office for European Patent No. 23797567.7 dated Mar. 11, 2026, 14 pages.
Ohzawa Seiya et al.: "Proximal oblique metatarsal osteotomy for hallux valgus using a plantar locking plate", Foot and Ankle Surgery, Jun. 17, 2017, vol. 24, No. 6, pp. 501-505, XP085546072, ISSN: 1268-7731, DOI: 10.1016/J.FAS.2017.05.013.

* cited by examiner

50

52

58

60

50

52

58

60

ORTHOPEDIC IMPLANTS, INSTRUMENT SYSTEMS AND METHODS OF USE

CROSS REFERENCE TO RELATED APPLICATION

This application is a bypass continuation of PCT Application No. PCT/US2023/066347, filed Apr. 28, 2023, and entitled "Orthopedic Implants, Instruments System and Methods of Use," which claims benefit of priority of U.S. Provisional Patent Application No. 63/363,724, filed on Apr. 28, 2022, and entitled "Orthopedic Implants" and U.S. Provisional Patent Application No. 63/366,184, filed on Jun. 10, 2022 and entitled "Instrument and Method for Biologic Implants" the disclosures of which are all hereby incorporated herein by reference in their entirety.

TECHNICAL FIELD

The present disclosure relates to implants, devices, and methods associated with performing orthopedic procedures. The present disclosure relates to podiatric and orthopedic implants and surgery related to arthroplasty, arthrodesis, arthroeresis and/or osteotomies of joints in the foot/ankle and/or procedures incorporating surrounding bones/soft tissue.

BACKGROUND OF THE INVENTION

Many currently available implants, devices, and methods for addressing bone, soft tissue, and joint trauma (acute and chronic, e.g., defect, gradual deterioration, etc.) do not completely address the needs of patients. Additionally, many currently available implants, devices, and methods for addressing joint trauma fail to account for properties of joint anatomy and associated mechanical and kinematic movement patterns/capabilities.

SUMMARY OF THE INVENTION

One aspect of the present disclosure is directed toward an orthopedic implant, for example a several embodiments of a bone plate. The implant includes an upper portion, a central portion having a greater lateral dimension than that of the upper portion, and a lower portion having a greater lateral dimension than the central portion. The upper portion, the central portion and the lower portion may also include at least one fixation aperture. The upper portion, the central portion and the lower portion may also be curved or non-linear in at least one plane.

According to one aspect of the present disclosure, the upper portion of the implant includes at least one opening extending from a top surface through to a bottom surface and configured to receive a fastener therethrough.

According to one aspect of the present disclosure, the central portion does not include any openings.

According to one aspect of the present disclosure, the lower portion includes at least one opening extending from a top surface through to a bottom surface and configured to receive a fastener therethrough.

According to one aspect of the present disclosure, the upper portion is non-linear and/or curved in at least one plane.

According to one aspect of the present disclosure, the central portion is non-linear and/or curved in at least one plane.

According to one aspect of the present disclosure, the lower portion is non-linear and/or curved in at least one plane.

According to one aspect of the present disclosure, the upper portion includes a slot extending from a top surface through to the bottom surface and configured to receive a fastener therethrough.

Another aspect of the present disclosure is directed toward orthopedic instruments. According to one aspect of the present disclosure, an orthopedic instrument that includes a body having a housing. The body further includes a platform configured to receive an implant, at least one retention mechanism configured to retain the implant at least partially on the platform, and an adjustment mechanism configured to adjust a height of at least a portion of the platform relative to a top surface of the housing. The instrument also includes a lid hingedly coupled with the housing, wherein the top surface of the housing and the lid define a cut slot configured to receive at least a portion of a cutting instrument.

According to one aspect of the present disclosure, the implant is a biological graft implant.

According to one aspect of the present disclosure, the implant has a substantially wedge-shaped geometry.

According to one aspect of the present disclosure, the at least one retention mechanism includes a pair of retention mechanisms configured to contact the implant on opposite sides of the implant.

According to one aspect of the present disclosure, the lid includes a window coupled with the lid, wherein the window is transparent.

According to one aspect of the present disclosure, the instrument includes at least one actuator positioned at least partially within the housing, wherein at least a first portion of the at least one actuator extends laterally through an opening in the lateral wall of the housing and at least a second portion of the at least one actuator extends vertically through an opening in the plate.

According to one aspect of the present disclosure, the at least one actuator is a pair of actuators positioned on opposite lateral sides of the housing.

According to one aspect of the present disclosure, each of the actuators is configured to releasably engage the lid so as to retain the lid in a closed position.

According to one aspect of the present disclosure, manipulation of the actuators disengages the actuators from the lid.

According to one aspect of the present disclosure, the lid includes a button releasably coupled with an engagement element.

According to one aspect of the present disclosure, manipulation of the button biases the engagement element such that the engagement element contacts the implant so as to retain the implant in a desired position.

Another aspect of the present disclosure is directed to a surgical system. The system includes an instrument including a body, with the body having a housing, a platform configured to receive a biologic implant, at least one retention mechanism configured to retain the biologic implant at least partially on the platform, an adjustment mechanism configured to adjust a height of at least a portion of the platform relative to a top surface of the housing, and a lid hingedly coupled with the housing, wherein the top surface of the housing and the lid define a cut slot configured to receive at least a portion of a cutting instrument. The system also includes a first implant configured to be reshaped within the housing of the instrument, and a second implant.

BRIEF DESCRIPTION OF THE DRAWINGS

The accompanying drawings, which are incorporated in and constitute a part of the specification, illustrate embodiments of the inventions and together with the detailed description herein, serve to explain the principles of the inventions. It is emphasized that, in accordance with the standard practice in the industry, various features may or may not be drawn to scale. In fact, the dimensions of the various features may be arbitrarily increased or reduced for clarity of discussion. The drawings are only for purposes of illustrating embodiments of inventions of the disclosure and are not to be construed as limiting the inventions.

Figure 1:
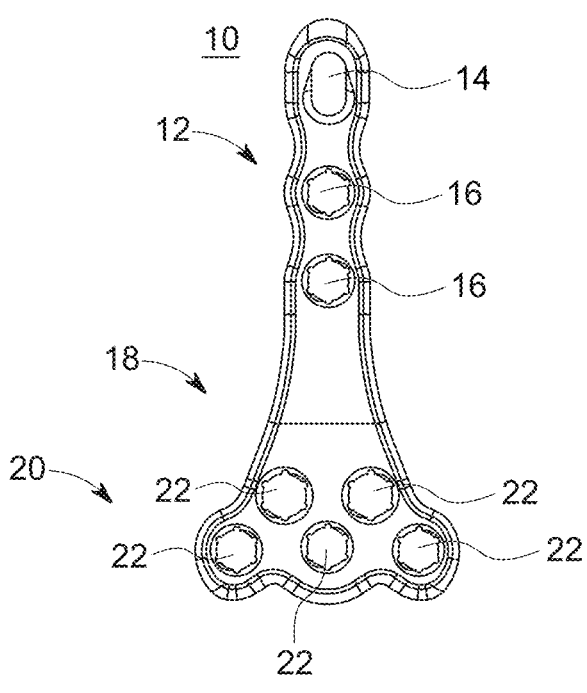
FIG. 1 is a front view of an orthopedic implant, in accordance with the present disclosure.
Figure 2:
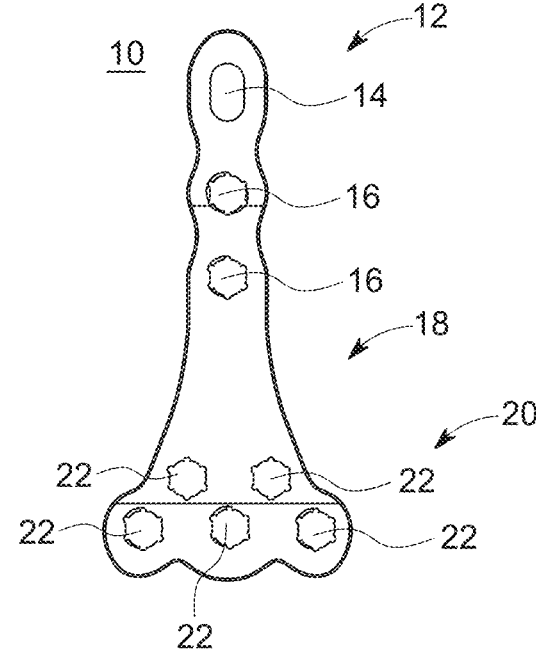
FIG. 2 is a rear view of the orthopedic implant of FIG. 1, in accordance with the present disclosure.
Figure 3:
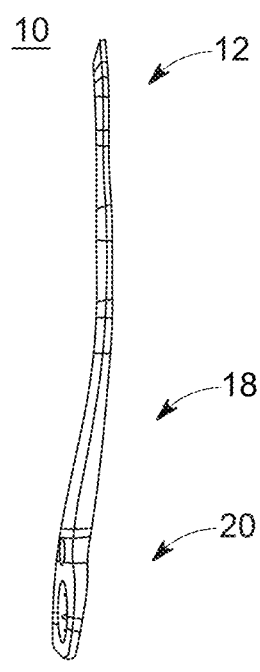
FIG. 3 is a first side view of the orthopedic implant of FIG. 1, in accordance with the present disclosure.
Figure 4:
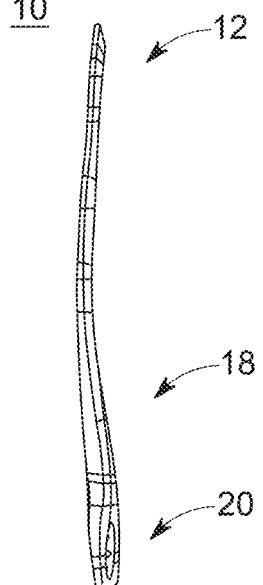
FIG. 4 is a second side view of the orthopedic implant of FIG. 1, in accordance with the present disclosure.
Figures 5, 6:
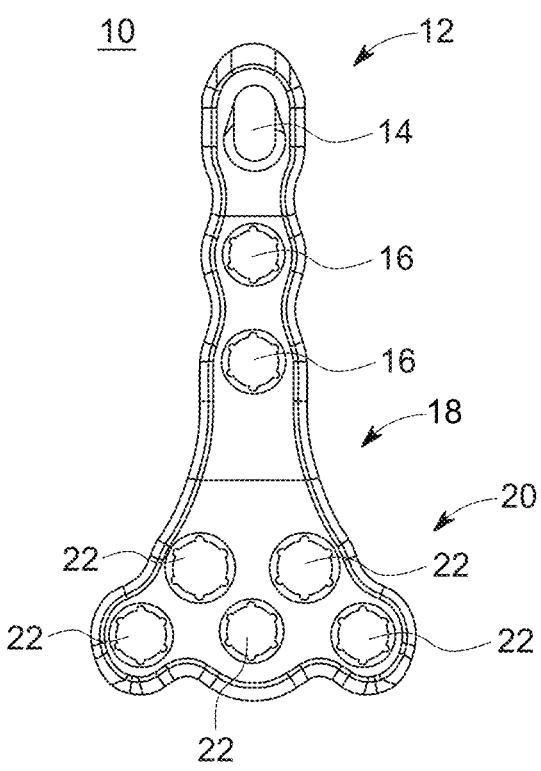
FIG. 5 is a front view of an orthopedic implant, in accordance with the present disclosure.
FIG. 6 is a rear view of the orthopedic implant of FIG. 5, in accordance with the present disclosure.
Figure 7:
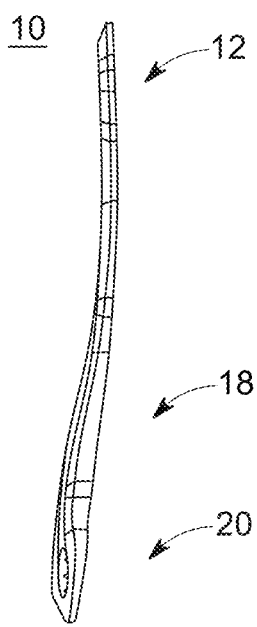
FIG. 7 is a first side view of the orthopedic implant of FIG. 5, in accordance with the present disclosure.
Figure 8:
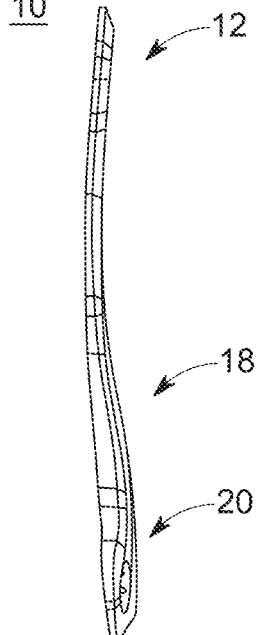
FIG. 8 is a second side view of the orthopedic implant of FIG. 5, in accordance with the present disclosure.
Figure 9:
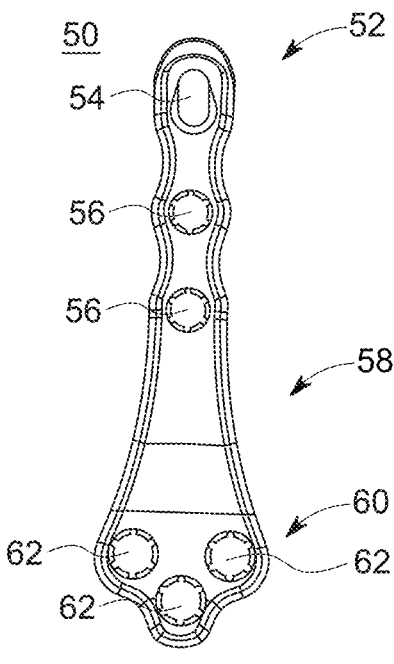
FIG. 9 is a front view of an orthopedic implant, in accordance with the present disclosure.
Figure 10:
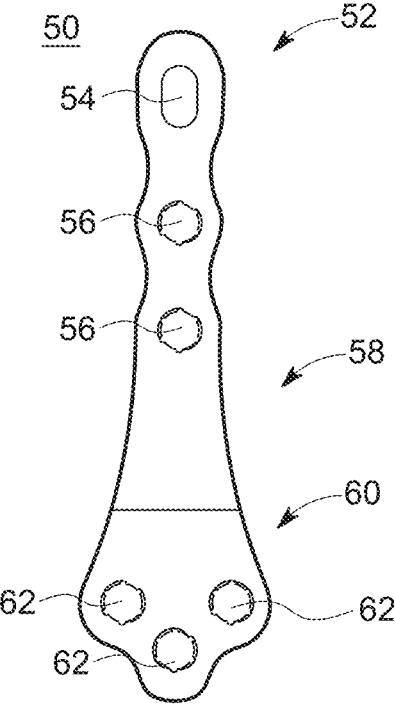
FIG. 10 is a rear view of the orthopedic implant of FIG. 9, in accordance with the present disclosure.
Figure 11:
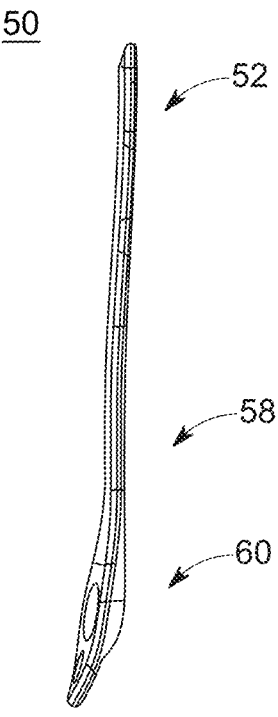
FIG. 11 is a first side view of the orthopedic implant of FIG. 9, in accordance with the present disclosure.
Figure 12:
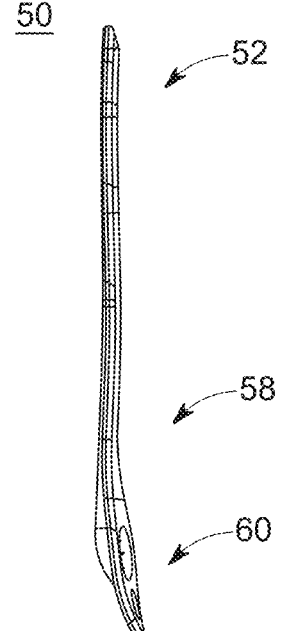
FIG. 12 is a second side view of the orthopedic implant of FIG. 9, in accordance with the present disclosure.
Figure 13:
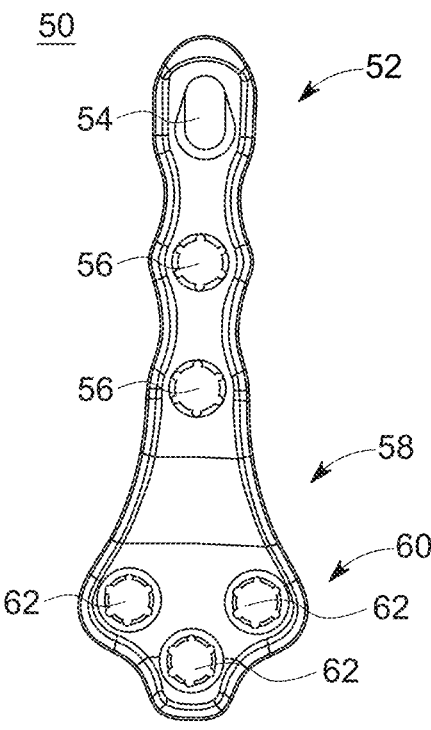
FIG. 13 is a front view of an orthopedic implant, in accordance with the present disclosure.
Figure 14:
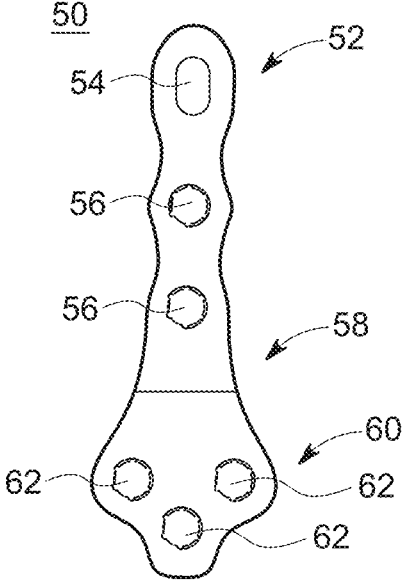
FIG. 14 is a rear view of the orthopedic implant of FIG. 13, in accordance with the present disclosure.
Figure 15:
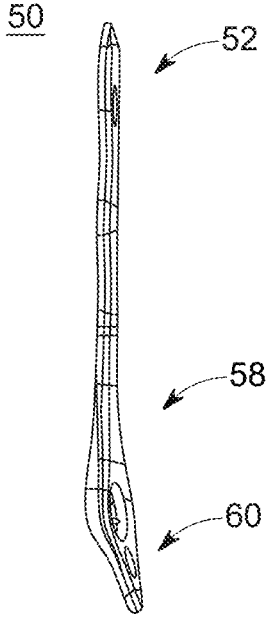
FIG. 15 is a first side view of the orthopedic implant of FIG. 13, in accordance with the present disclosure.
Figure 16:
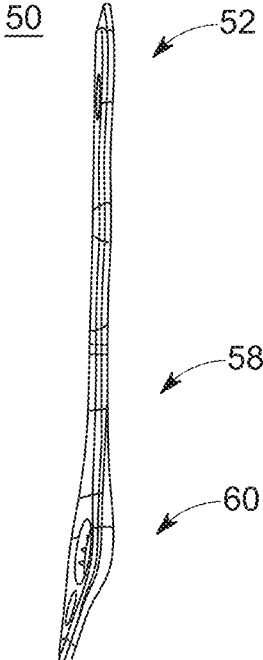
FIG. 16 is a second side view of the orthopedic implant of FIG. 13, in accordance with the present disclosure.

DETAILED DESCRIPTION OF THE
INVENTION

In this detailed description and the following claims, the words proximal, distal, anterior, or plantar, posterior, or dorsal, medial, lateral, superior, and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation, and methods are described herein with reference to use with the bones of the foot, the bones of the foot, ankle and lower leg may be used to describe the surfaces, positions, directions or orientations of the implants, devices, instrumentation, and methods. Further, the implants, devices, instrumentation, and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation, and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation, and methods, and the aspects, components, features and the like thereof, described herein with respect to the right foot may be mirrored so that they likewise function with the left foot. Further, the implants, devices, instrumentation, and methods, and the aspects, components, features and the like thereof, disclosed herein are described with respect to the foot for brevity purposes, but it should be understood that the implants, devices, instrumentation, and methods may be used with other bones of the body having similar structures.

Referring to the drawings, wherein like reference numerals are used to indicate like or analogous components throughout the several views, and with particular reference to FIGS. 1-24, orthopedic implants (e.g., plates) are shown. The implants are shown to include various portions (e.g., upper, central, lower, etc.) having various lateral dimensions that may be greater than, less than, or equal to one another. Similarly, the aforementioned portions may also include various thicknesses that may be greater than, less than, or equal to one another. Further, the aforementioned portions may also be curved and/or non-planar relative to each other to approximate the external contour of the adjacent bone surface. The implants shown may be implemented in conjunction with other implant components and/or systems, for example wedges of various sizes/shapes, trial instruments corresponding to the wedges, and other instruments common to orthopedic procedures. In some aspects, the implants shown may include a central portion (shown herein as a substantially solid portion, e.g., free of apertures) configured to span an osteotomy site (in which a wedge or other implant may be placed). The implants may also include upper and lower portions including one or more fixation apertures configured for coupling the implant with a bone of a patient (e.g., a tibia) on opposite sides of the osteotomy site so as to retain the wedge within a desired position (e.g., within the osteotomy site).

Referring now to FIGS. 1-8, an orthopedic implant 10 is shown, according to an exemplary embodiment. The implant 10 as shown is an orthopedic bone plate configured to releasably couple with one or more bones or bony segments of a patient via one or more fasteners (e.g., screws, etc.). As shown, the implant 10 includes an upper portion 12, a central portion 18, and a lower portion 20. The upper and lower portions 12 and 20, respectively, are positioned opposite the central portion 18 from one another. As shown, the lower portion 20 has a lateral dimension greater than the central and upper portions 18 and 12, and the central portion 18 has a greater lateral dimension than the upper portion 12. Moving from the lower portion 20 upward toward the upper portion 12, the implant 10 is shown to be tapered from a greater lateral width to a lesser lateral width.

The upper portion 12 is shown to include a slot 14 positioned at an uppermost portion thereof and, as shown in the exemplary embodiment of FIGS. 1-8, is positioned adjacent a terminal end of the upper portion 12. In some aspects, the slot 14 may be configured to receive a fastener therein and therethrough so as to facilitate coupling with a bone/bony segment. Further, in some aspects the slot 14 may be configured as a compression slot such that a fastener may be inserted therein and therethrough so as to couple with one or more bones/bony segments and apply a compressive force across the bones/bony segments. The upper portion 12 also includes at least one opening 16 configured to receive a fastener therein and therethrough. As shown in FIGS. 1-8, the at least one opening 16 is a pair of openings adjacent one another. It should be understood that in some aspects, the implant 10 may be offered in various sizes/lengths and, accordingly, one or more of the slot 14 and/or openings 16 may be positioned about the upper portion 12.

The central portion 18 is shown to be integral with the upper and lower portions 12, 20 and is further shown to include a marking thereon. In some aspects, the marking may include various sizing, SKU, or other information relevant to the implant 10. As shown in at least FIGS. 3-4, the central portion 18 includes a tapered thickness, with a lesser thickness adjacent the upper portion 12 and a greater thickness adjacent the lower portion 20. As shown, the central portion 18 does not include any openings or slots, but in some aspects the central portion 18 may include one or more features configured to facilitate coupling of the implant 10 with one or more bones/bony segments. Further, in some aspects, the central portion 10 may be configured to span an osteotomy site in a bone or between bony segments which in some aspects, may include a volume filled by a graft (e.g., a wedge) or other additional implant.

The lower portion 20 is shown to be integral with the central portion 18 of the implant 10. Further, the lower portion 20 is shown to include at least one opening 22 configured to receive a fastener therein and therethrough so as to facilitate coupling with one or more bones or bony segments. In some aspects, the openings 22 may be the same as or similar to the openings 16 of the upper portion 12. As shown, the lower portion 20 includes a total of five openings 22 positioned in two offset rows (three in a bottom row, two in a top). However, in some aspects, the openings 22 may be positioned alternatively about the lower portion 22 and may also be present in varying quantities. In some embodiments, the lower portion 20 may include a slot, for example a slot the same as or similar to the slot 14 of the upper portion 12.

As the implant 10 may be sized to accommodate various procedures or sizing in the bones/anatomy of patients, the upper, central, and lower portions 12, 18, 20 may be come in various sizes. For example, in some aspects the central portion 18 may have a greater or lesser length than that shown relative to the upper and lower portions 12, 20. Further, in some aspects the positioning, quantity, and spacing of the slot 14 as well as the openings 16, 22 may vary according to the size of the implant 10 and the various portions thereof.

Referring now to FIGS. 9-16, an orthopedic implant 50 is shown, according to an exemplary embodiment. The implant 50 as shown is an orthopedic bone plate configured to releasably couple with one or more bones or bony segments of a patient via one or more fasteners (e.g., screws, etc.). As shown, the implant 50 includes an upper portion 52, a central portion 58, and a lower portion 60. The upper and lower portions 52 and 60, respectively, are positioned opposite the central portion 58 from one another. As shown, the lower portion 60 has a lateral dimension (at its widest point) that is greater than that of the central and upper portions 58 and 52, and the central portion 58 has a greater lateral dimension (at its widest point) than the upper portion 52. Moving from the lower portion 60 upward toward the upper portion 52, the implant 50 is shown to be tapered from a greater lateral width to a lesser lateral width (when considering each portion at its widest point).

The upper portion 52 is shown to include a slot 54 positioned at an uppermost portion thereof and, as shown in the exemplary embodiment of FIGS. 9-16, is positioned adjacent a terminal end of the upper portion 52. In some aspects, the slot 54 may be configured to receive a fastener therein and therethrough so as to facilitate coupling with a bone or bony segment. Further, in some aspects, the slot 54 may be configured as a compression slot such that a fastener may be inserted therein and therethrough so as to couple with one or more bones/bony segments and apply a compressive force across the bones/bony segments. The upper portion 52 also includes at least one opening 56 configured to receive a fastener therein and therethrough. As shown in FIGS. 9-16, the at least one opening 56 is a pair of openings in line with and spaced from one another. It should be understood that in some aspects, the implant 50 may be offered in various sizes/lengths and, accordingly, one or more of the slot 54 and/or openings 56 may be positioned about the upper portion 52.

The central portion 58 is shown to be integral with the upper and lower portions 52, 60 and is further shown to include a marking thereon. In some aspects, the marking may include various sizing notations, SKU, or other information relevant to the implant 50. As shown, the central portion 58 does not include any openings or slots, but in some aspects the central portion 58 may include one or more features configured to facilitate coupling of the implant 50 with one or more bones or bony segments. Further, in some aspects, the central portion 50 may be configured to span an osteotomy site in a bone or connect bony segments which in some aspects, may include a volume filled by a graft (e.g., a wedge) or other additional implant.

The lower portion 60 is shown to be integral with the central portion 58 of the implant 50. Further, the lower portion 60 is shown to include at least one opening 62 configured to receive a fastener therein and therethrough so as to facilitate coupling with one or more bones or bony segments. As shown in FIGS. 9-16, the lower portion 60 has a taper to its terminal end, then widens when moving in the direction of the central portion 58. In some aspects, the openings 62 may be the same as or similar to the openings 56 of the upper portion 52. As shown, the lower portion 60 includes a total of three openings 62 positioned in two offset rows (one in a bottom row, two in a top). However, in some aspects the openings 62 may be positioned alternatively about the lower portion 62 and may also be present in varying quantities. In some embodiments, the lower portion 60 may include a slot, for example a slot that is the same as or similar to the slot 54 of the upper portion 52.

As the implant 50 may be sized to accommodate various procedures or sizing in the bones/anatomy of patients, the upper, central, and lower portions 52, 58, 60 may be of various lengths or thicknesses. For example, in some aspects the central portion 58 may have a greater or lesser length than that shown relative to the upper and lower portions 52, 60. Further, in some aspects the positioning, quantity, and spacing of the slot 54 as well as the openings 56, 62 may vary according to the size of the implant 50 and the various portions thereof.

Referring now to FIGS. 17-24, an orthopedic implant 70 is shown, according to an exemplary embodiment. The implant 70 as shown is an orthopedic bone plate configured to releasably couple with one or more bones or bony segments of a patient via one or more fasteners (e.g., screws, etc.). As shown, the implant 70 includes an upper portion 72, a central portion 78, and a lower portion 80. The upper and lower portions 72 and 80, respectively, are positioned opposite the central portion 78 from one another. As shown, the lower portion 80 has a lateral dimension greater than the central and upper portions 78 and 72, and the central portion 76 has a greater lateral dimension than the upper portion 72. Moving from the lower portion 80 upward toward the upper portion 72, the implant 70 is shown to be tapered from a greater lateral width to a lesser lateral width.

Figure 17:
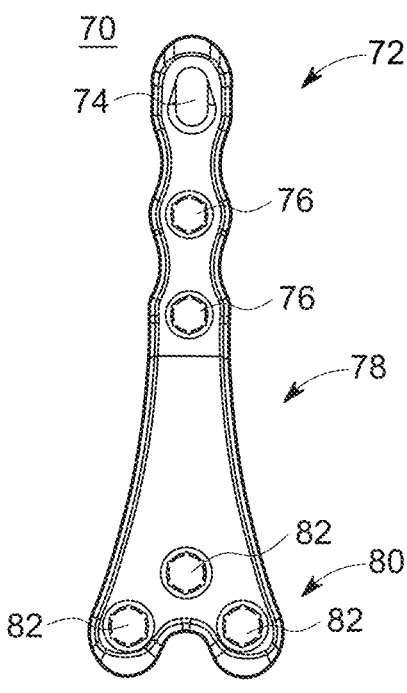
FIG. 17 is a front view of an orthopedic implant, in accordance with the present disclosure.
Figure 18:
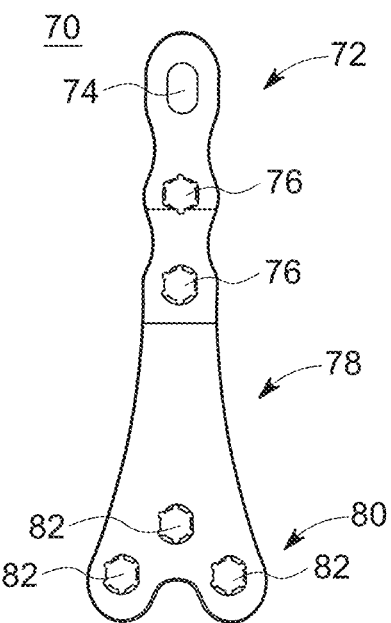
FIG. 18 is a rear view of the orthopedic implant of FIG. 17, in accordance with the present disclosure.
Figure 19:
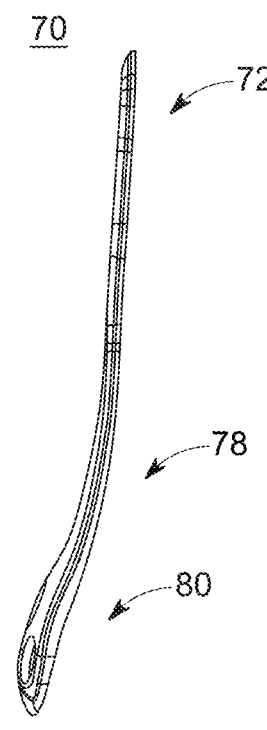
FIG. 19 is a first side view of the orthopedic implant of FIG. 17, in accordance with the present disclosure.
Figure 20:
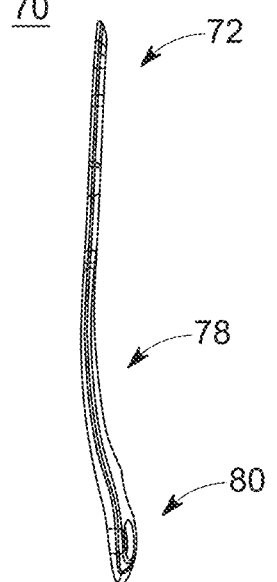
FIG. 20 is a second side view of the orthopedic implant of FIG. 17, in accordance with the present disclosure.
Figure 21:
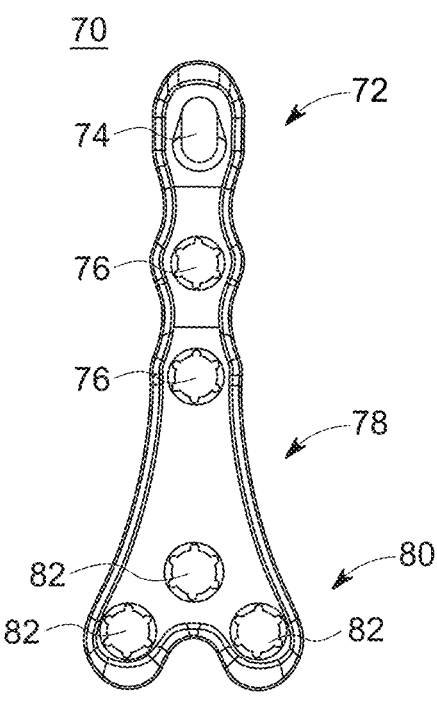
FIG. 21 is a front view of an orthopedic implant, in accordance with the present disclosure.
Figure 22:
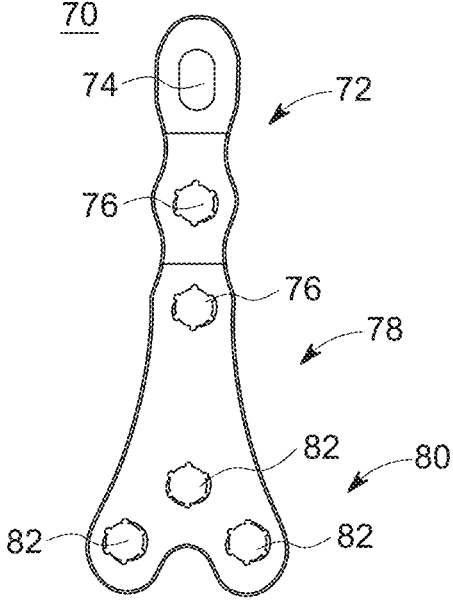
FIG. 22 is a rear view of the orthopedic implant of FIG. 21, in accordance with the present disclosure.
Figure 23:
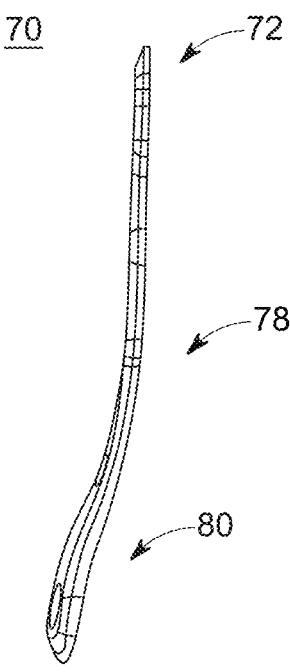
FIG. 23 is a first side view of the orthopedic implant of FIG. 21, in accordance with the present disclosure.
Figure 24:
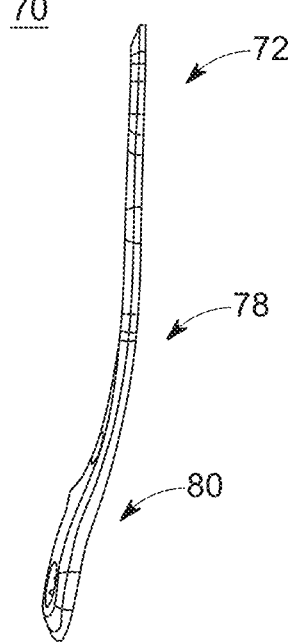
FIG. 24 is a second side view of the orthopedic implant of FIG. 21, in accordance with the present disclosure.
Figure 25:
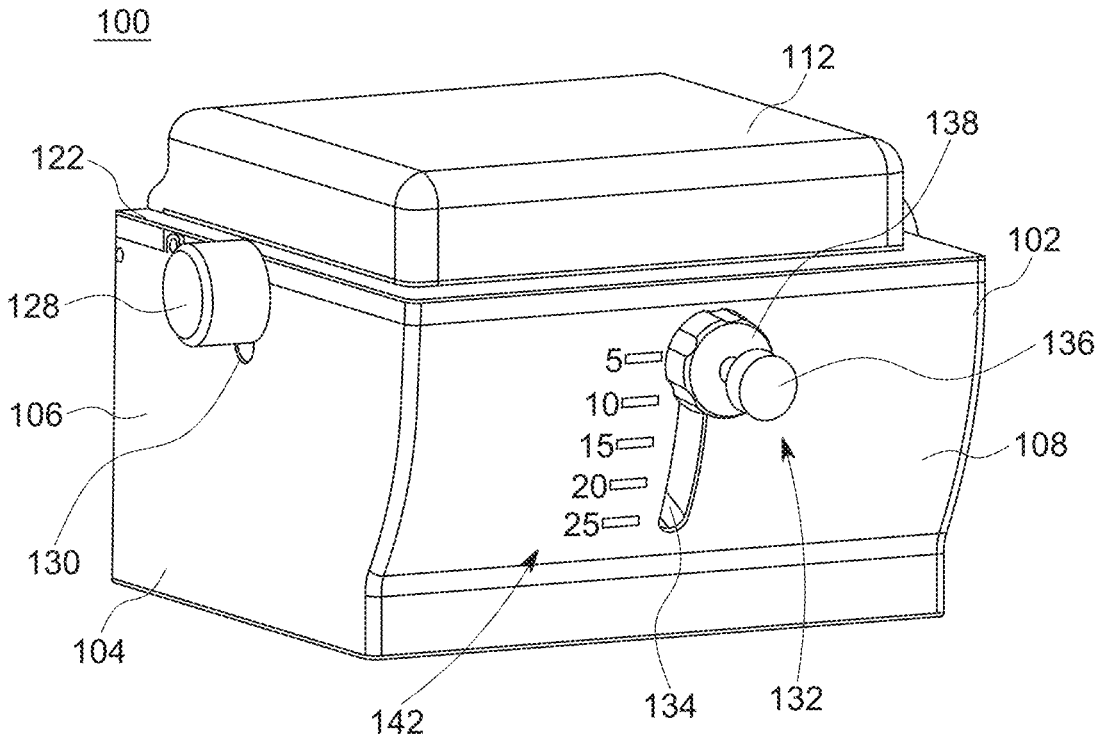
FIG. 25 is a front perspective view of an orthopedic instrument, in accordance with the present disclosure.
Figure 26:
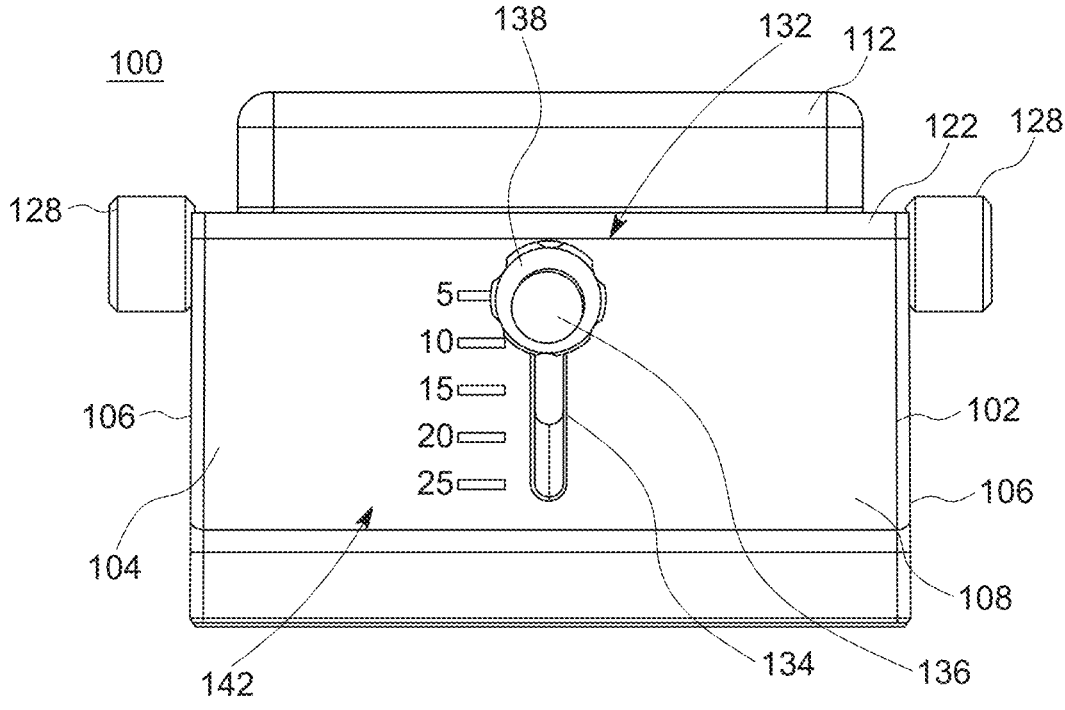
FIG. 26 is a front view of the orthopedic instrument of FIG. 25, in accordance with the present disclosure.
Figure 27:
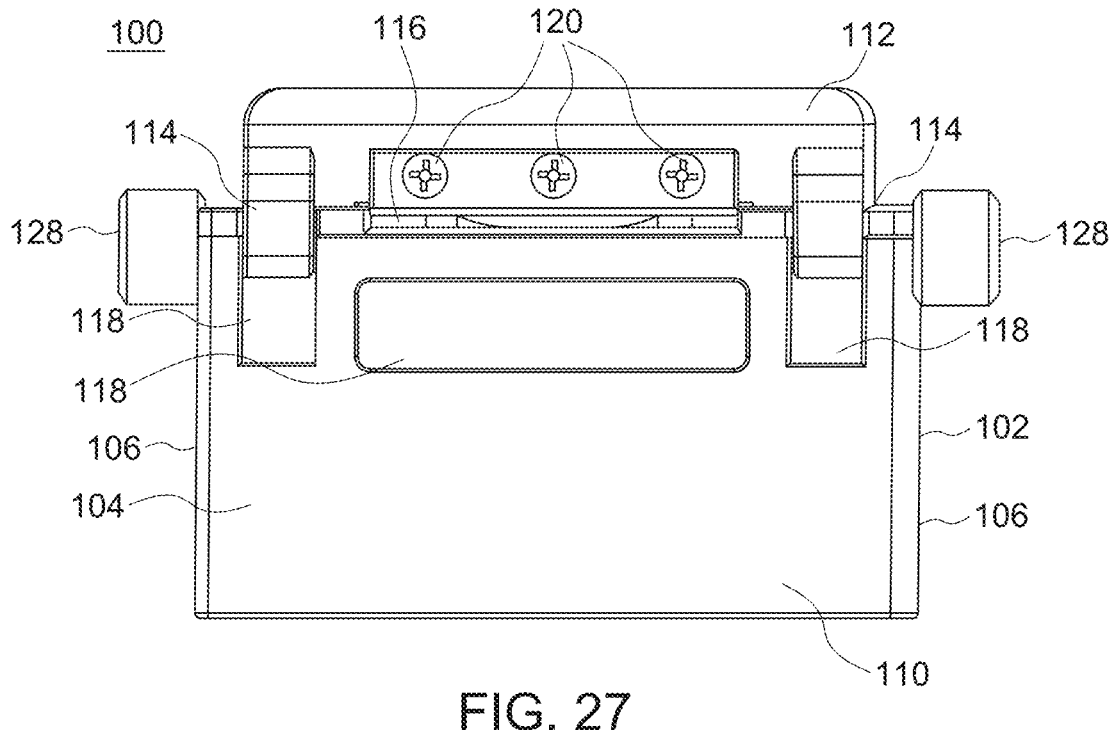
FIG. 27 is a rear view of the orthopedic instrument of FIG. 25, in accordance with the present disclosure.
Figure 28:
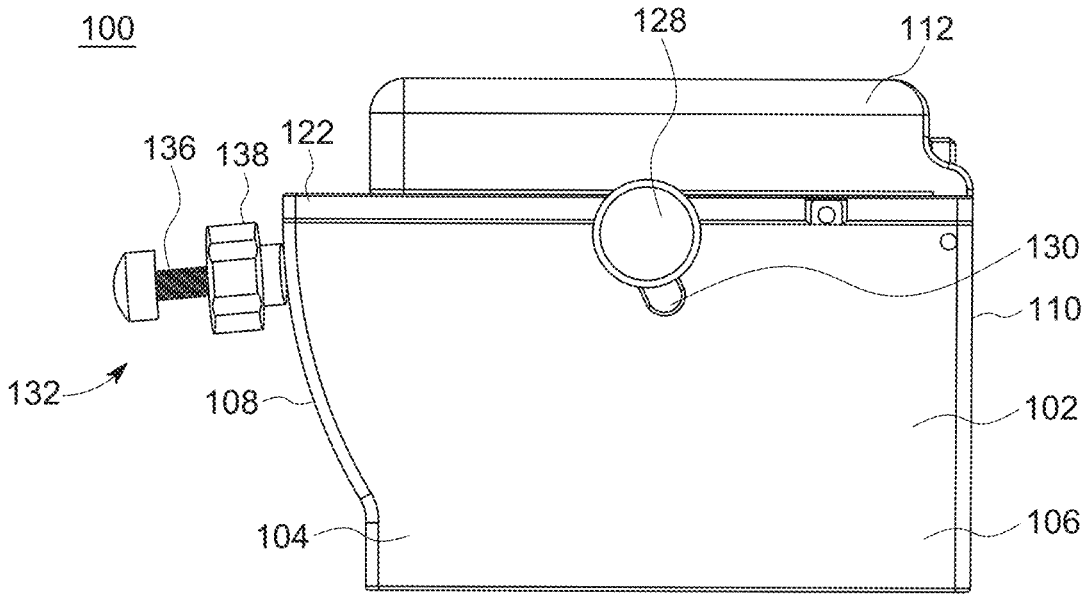
FIG. 28 is a first side view of the orthopedic instrument of FIG. 25, in accordance with the present disclosure.
Figure 29:
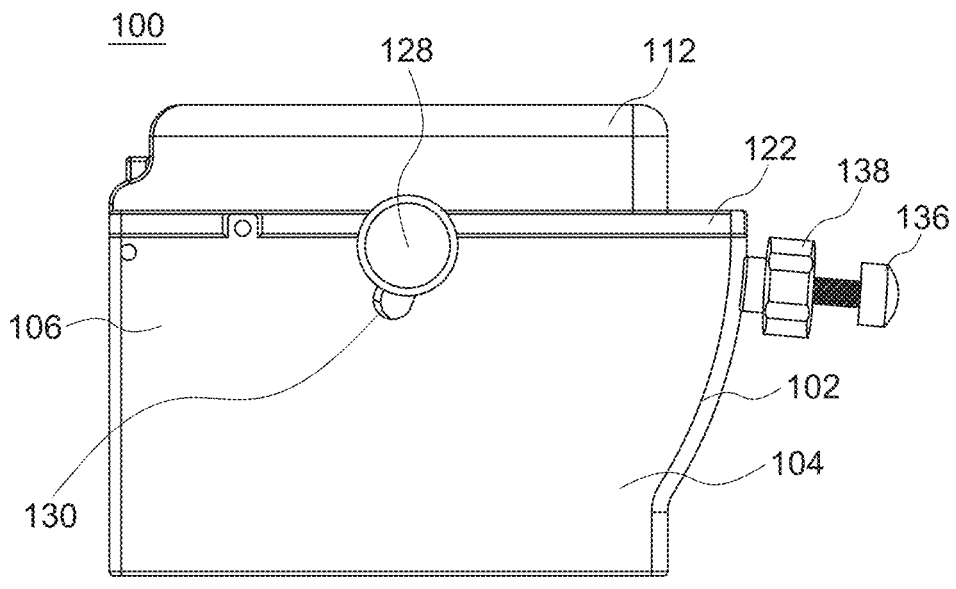
FIG. 29 is a second side view of the orthopedic instrument of FIG. 25, in accordance with the present disclosure.
Figure 30:
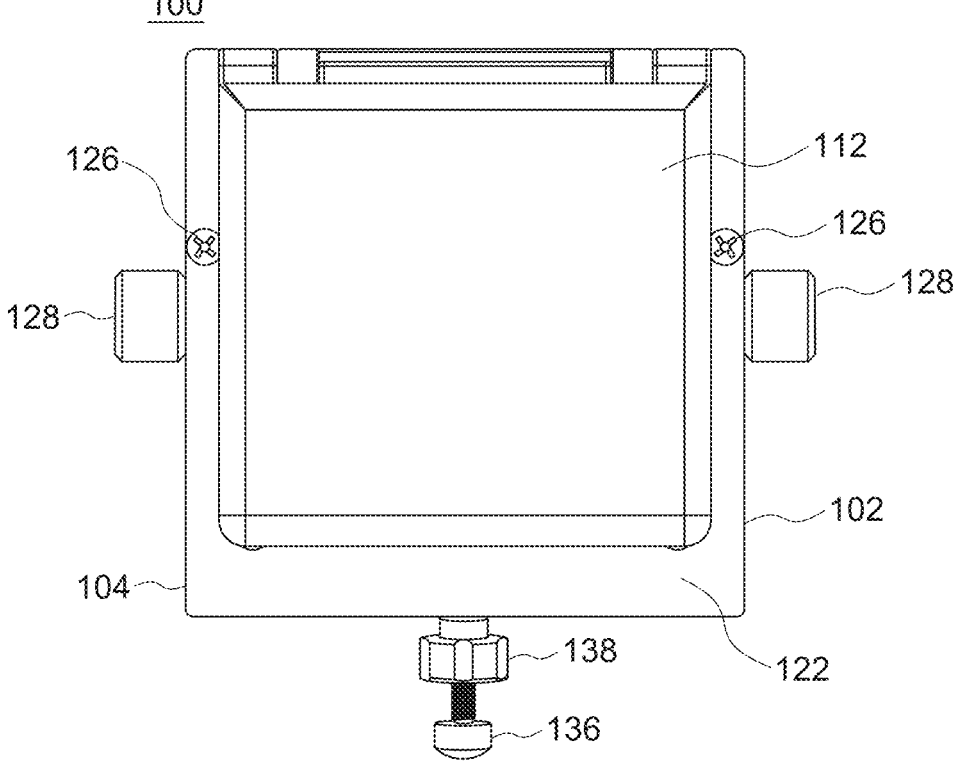
FIG. 30 is a top view of the orthopedic instrument of FIG. 25, in accordance with the present disclosure.
Figure 31:
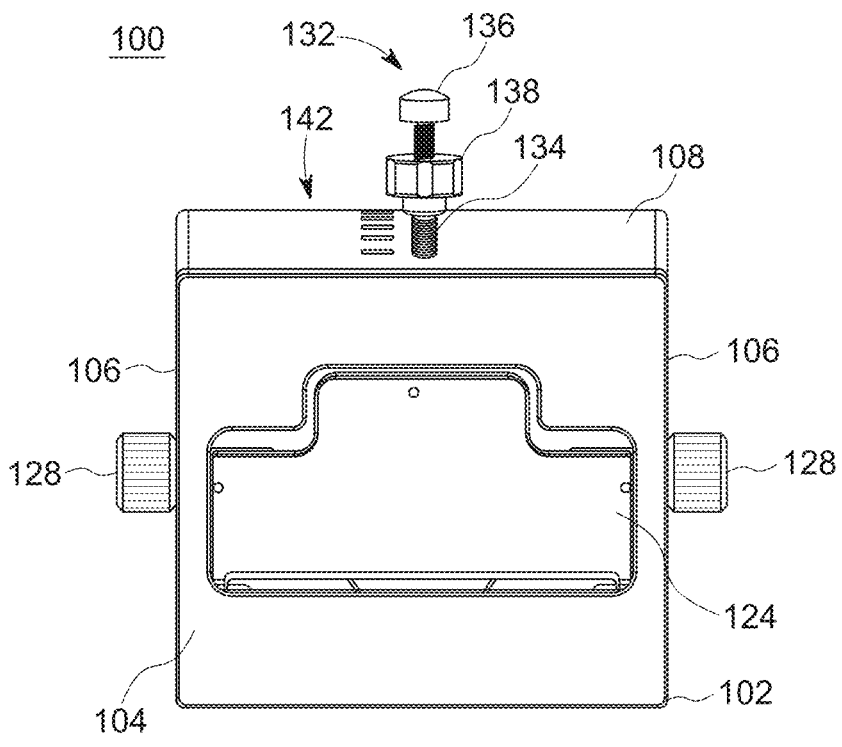
FIG. 31 is a bottom view of the orthopedic instrument of FIG. 25, in accordance with the present disclosure.
Figure 32:
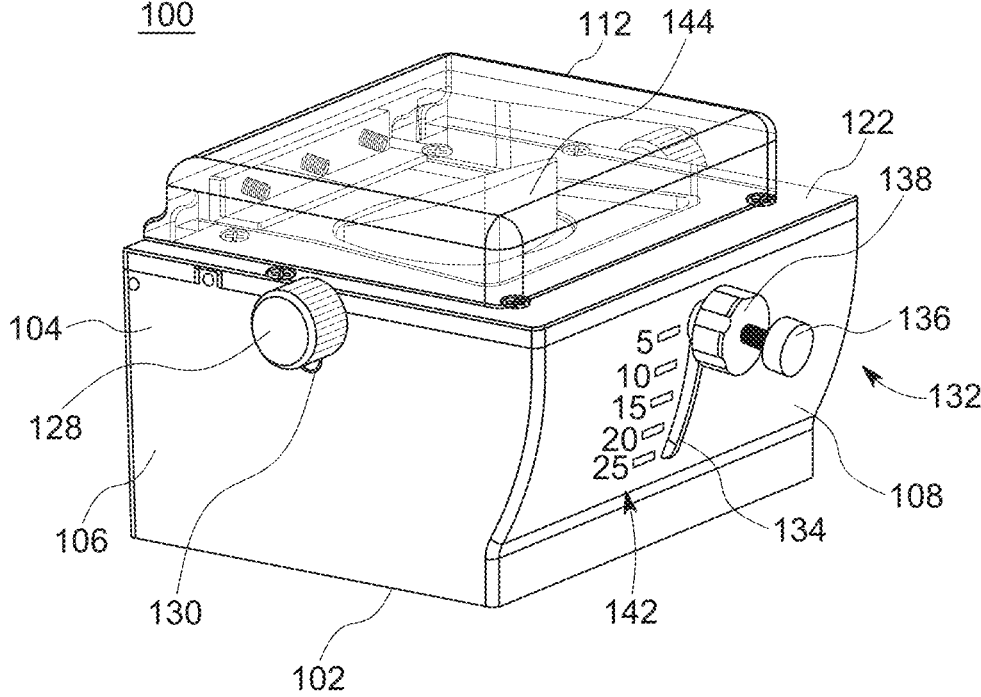
FIG. 32 is an alternate front perspective view of the orthopedic instrument of FIG. 25 showing a transparent lid, in accordance with the present disclosure.
Figure 33:
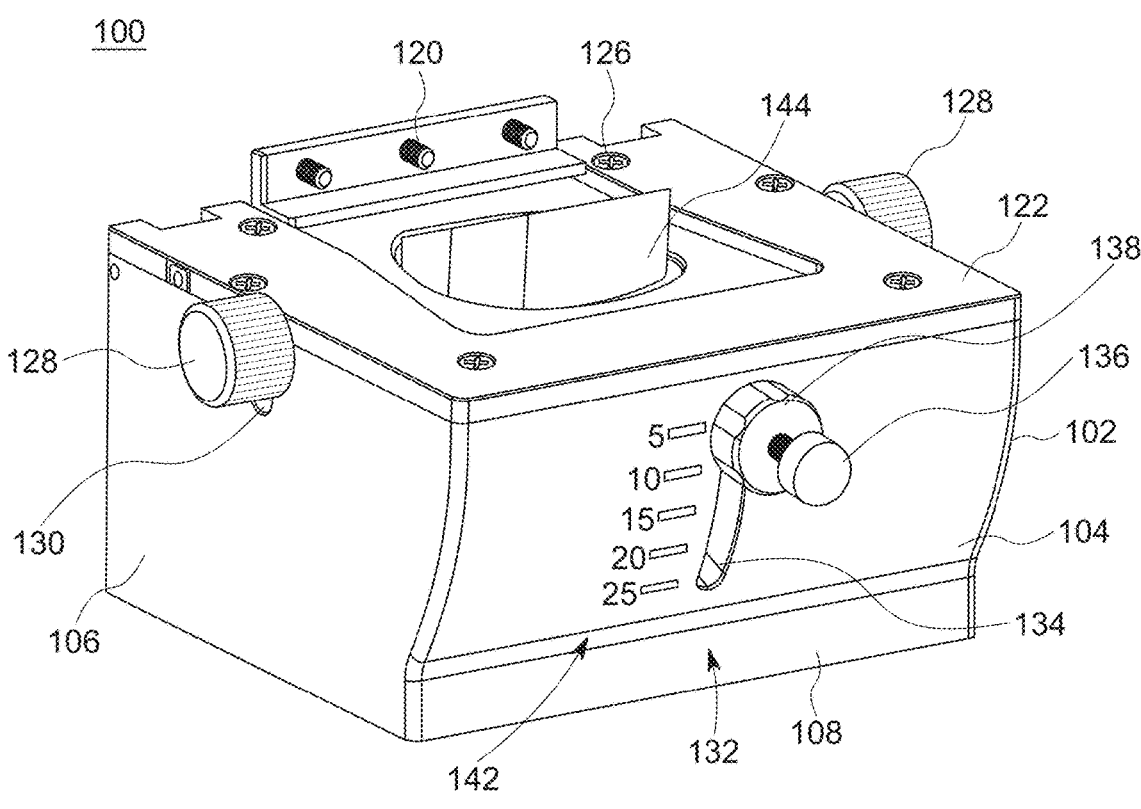
FIG. 33 is a front perspective view of a portion of the orthopedic instrument of FIG. 25, in accordance with the present disclosure.

The upper portion 72 is shown to include a slot 74 positioned at an uppermost portion thereof and, as shown in the exemplary embodiment of FIGS. 17-24, is positioned adjacent a terminal end of the upper portion 72. In some aspects, the slot 74 may be configured to receive a fastener therein and therethrough so as to facilitate coupling with a bone or/bony segment. Further, in some aspects the slot 74 may be configured as a compression slot such that a fastener may be inserted therein and therethrough so as to couple with one or more bones or bony segments and apply a compressive force across the bones or bony segments. The upper portion 72 also includes at least one opening 76 configured to receive a fastener therein and therethrough. As shown in FIGS. 17-18, the at least one opening 76 is a pair of openings in line with and spaced from one another. It should be understood that in some aspects, the implant 70 may be offered in various sizes/lengths and, accordingly, one or more of the slot 74 and/or openings 76 may be positioned about the upper portion 72.

The central portion 78 is shown to be integral with the upper and lower portions 72, 80 and is further shown to include a marking thereon. In some aspects, the marking may include various sizing designations, SKU, or other information relevant to the implant 70. As shown, the central portion 78 does not include any openings or slots, but in some aspects the central portion 78 may include one or more features configured to facilitate coupling of the implant 70 with one or more bones or bony segments. Further, in some aspects, the central portion 70 may be configured to span an osteotomy site in a bone or between bony segments which in some aspects, may include a volume filled by a graft (e.g., a wedge) or other additional implant.

The lower portion 80 is shown to be integral with the central portion 78 of the implant 70. Further, the lower portion 80 is shown to include at least one opening 82 configured to receive a fastener therein and therethrough so as to facilitate coupling with one or more bones/bony segments. As shown, the lower portion 80 includes a pair of lobes extending therefrom at a terminal end of the lower portion 80 and, in the exemplary embodiment of FIGS. 17-24, openings 82 are positioned within each of the lobes. In some aspects, the openings 82 may be the same as or similar to the openings 76 of the upper portion 72. As shown, the lower portion 80 includes a total of three openings 82 positioned in two offset rows (two in a bottom row, one in a top). However, in some aspects the openings 82 may be positioned alternatively about the lower portion 82 and may also be present in varying quantities. In some embodiments, the lower portion 80 may include a slot, for example a slot the same as or similar to the slot 74 of the upper portion 72.

As the implant 70 may be sized to accommodate various procedures or sizing in the bones/anatomy of patients, the upper, central, and lower portions 72, 78, 80 may be correspondingly variously sized. For example, in some aspects the central portion 78 may have a greater or lesser length than that shown relative to the upper and lower portions 72, 80. Further, in some aspects the positioning, quantity, and spacing of the slot 74 as well as the openings 76, 82 may vary according to the size of the implant 70 and the various portions thereof.

Referring now to FIGS. 25-43, an orthopedic instrument 100 system and components thereof are shown, according to various aspects of the present disclosure. In some aspects, the instrument 100 may be a component of a surgical kit or larger surgical system provided to a physician. For example, the instrument 100 may be a component of a kit/system including (but in no way limited to) one or more biologic implants (e.g., bone wedges or other graft implants), various fixation options and corresponding fasteners (e.g., plates, intramedullary (IM) nails, screws, etc.) as well as various other instrumentation common to orthopedic surgical procedures. In some aspects, a surgical kit may include one or more of the instrument 100, for example where various embodiments of the instrument 100 may be of varying sizes, shapes, and other geometries or be configured to accommodate biologic implants of various sizes, shapes, and other geometries.

The instrument 100 is shown to include a body 102 having a housing 104. As shown, the housing 104 is configured to have a substantially cube or box-shaped geometry, although in some aspects the housing 104 may have alternate geometries. The housing 104 includes a pair of lateral sides 106 separated by a front side 108 and a back side 110, where the lateral sides 106 are configured in a first set of parallel planes and the front and back sides 106, 110 are configured in a second set of parallel planes, with the first and second sets of parallel planes being substantially orthogonal to one another. The body 102 is further shown to include a plate 122 positioned in a plane substantially perpendicular to and above the planes of the lateral sides, front side, and back side 106, 108, 110. The plate 122 may be integral with one or more of the aforementioned sides of the housing 104 or, as shown in the exemplary embodiments herein, and may be releasably coupled with one or more components of the body 102 and/or housing 104 via one or more fasteners 120. In some aspects, the fasteners 120 may be configured to be received through one or more openings in the plate 122 and further received within one or more geometries of the body 102 and/or the housing 104 configured to be complimentary to the geometry of the one or more fasteners 120 (e.g., a bore or other opening with a threading complimentary to that of the fasteners 120). As shown, the fasteners 122 include, for example, a common Phillips-style interface configured to facilitate manipulation (e.g., installation or removal) via, for example, a similar Phillips-style instrument, however in various embodiments the fasteners 122 may include one or more alternate geometries (e.g., flathead, hexalobe, Torxx, etc.).

The instrument 100 is further shown to include a lid 112 configured to hingedly (and, in some embodiments, releasably) couple with an upper portion of the housing 104 via a pair of hinges 114. However, in some aspects the lid 112 may be hingedly coupled with the plate 122 and/or the housing 104. The lid 112 as shown is configured to be manipulated from open to closed (and closed to open positions) about the hinges 114, where the range of motion of the lid 112 may be a pivoting motion about a longitudinal axis extending through each of the hinges 114. Further, the lid 112 is shown to be coupled with a protrusion extending from the platform 122 (but may alternatively extend from the housing 104) via one or more fasteners 126 which, as shown, may be the same as or similar to the fasteners 120 (or may include one or more of the alternate embodiments as discussed with respect to the fasteners 120). The range of motion of the lid 112 may be constrained by the protrusion when in a coupled state therewith, which is to say that the range of motion of the lid 112, for example, may be at least 90-degrees (but may be greater or less), with the at least 90-degree range of motion existing between an upper surface of the plate 122 (with at least a portion of the bottom surface of the lid contacting at least a portion of the top surface of the plate; a "closed" position) and a surface of the protrusion positioned closest to the front side 108 of the housing 104 (with at least a portion of the top surface of the lid contacting at least a portion of the surface of the protrusion; an "open" position). In some aspects, the lid 112 may include an approximately 180-degree range of motion, or a greater range of motion. The back side 110 of the housing 104 is shown to include at least one depression 118 configured to receive at least a portion of the lid 112 when in an "open" position as previously defined. Accordingly, when in the "open" position, the depressions 118 may receive a portion of the lid 112 coupled with the hinges 114 and/or adjacent a portion of the lid 112 coupled with the hinges 114 so as to prevent the range of motion of the lid 112 being limited in a maximum "open" position by a mechanical stop including at least a portion of the lid 112 contacting at least a portion of the back side 110 of the housing 104.

Figure 34:
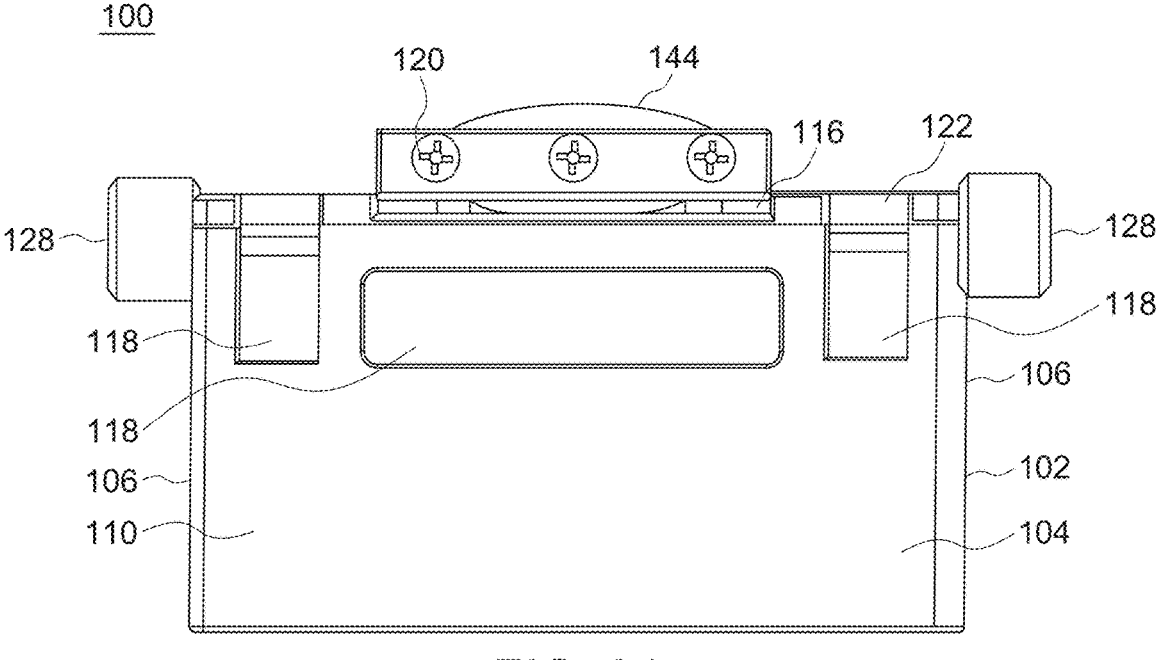
FIG. 34 is a rear view of a portion of the orthopedic instrument of FIG. 25, in accordance with the present disclosure.
Figures 35, 36:
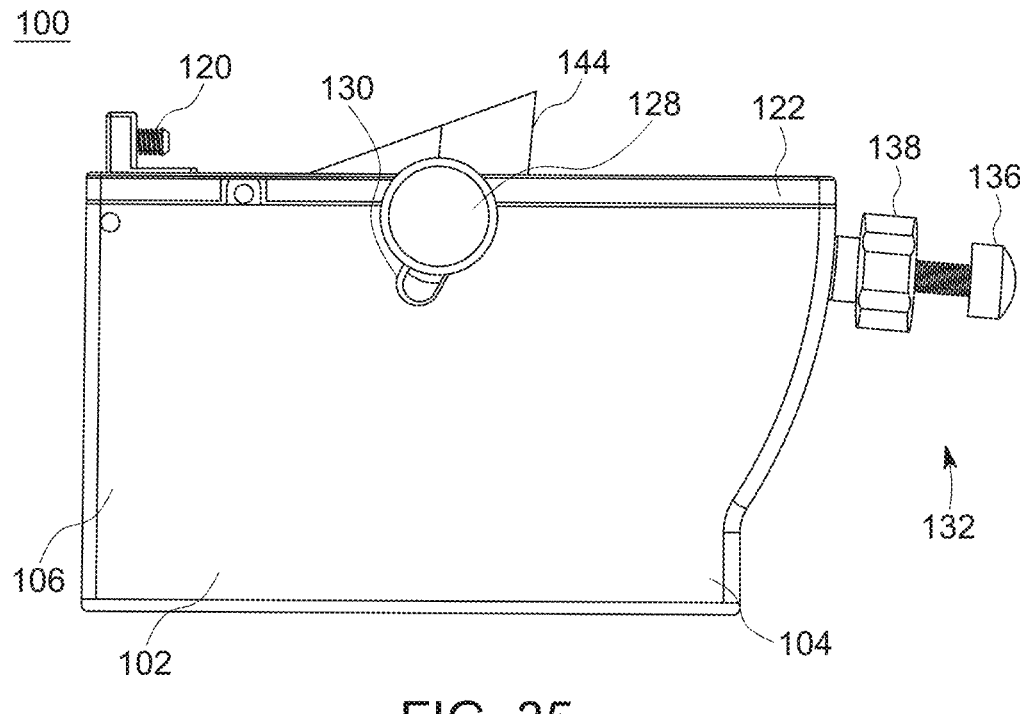
FIG. 35 is a first side view of a portion of the orthopedic instrument of FIG. 25, in accordance with the present disclosure.
FIG. 36 is a second side view a portion of the orthopedic instrument of FIG. 25, in accordance with the present disclosure.
Figure 37:
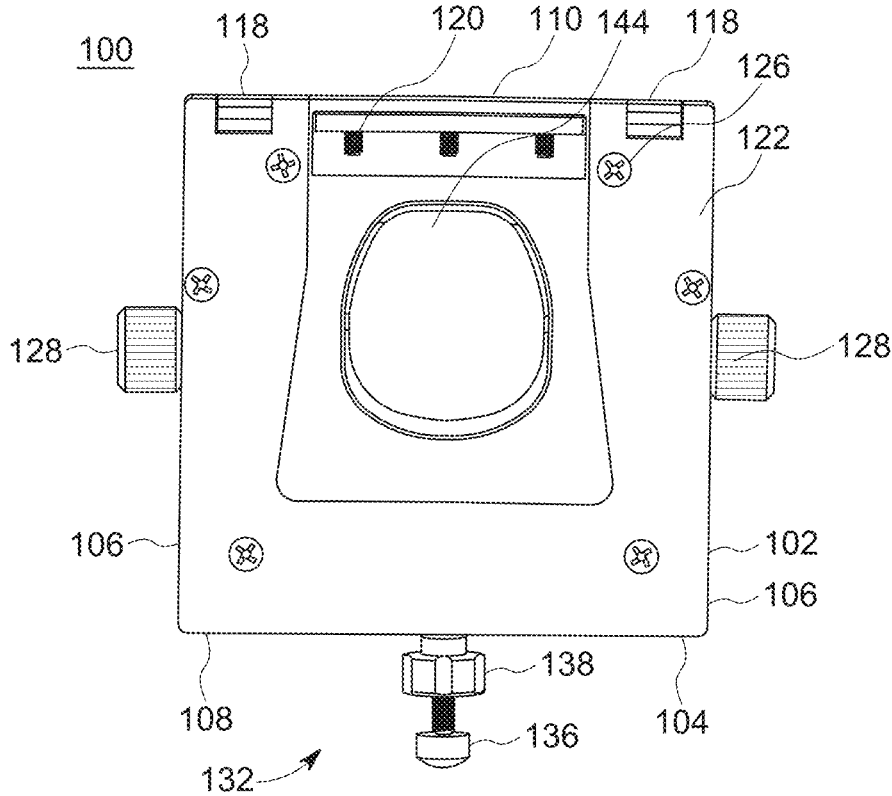
FIG. 37 is a top view of a portion of the orthopedic instrument system of FIG. 25, in accordance with the present disclosure.
Figure 38:
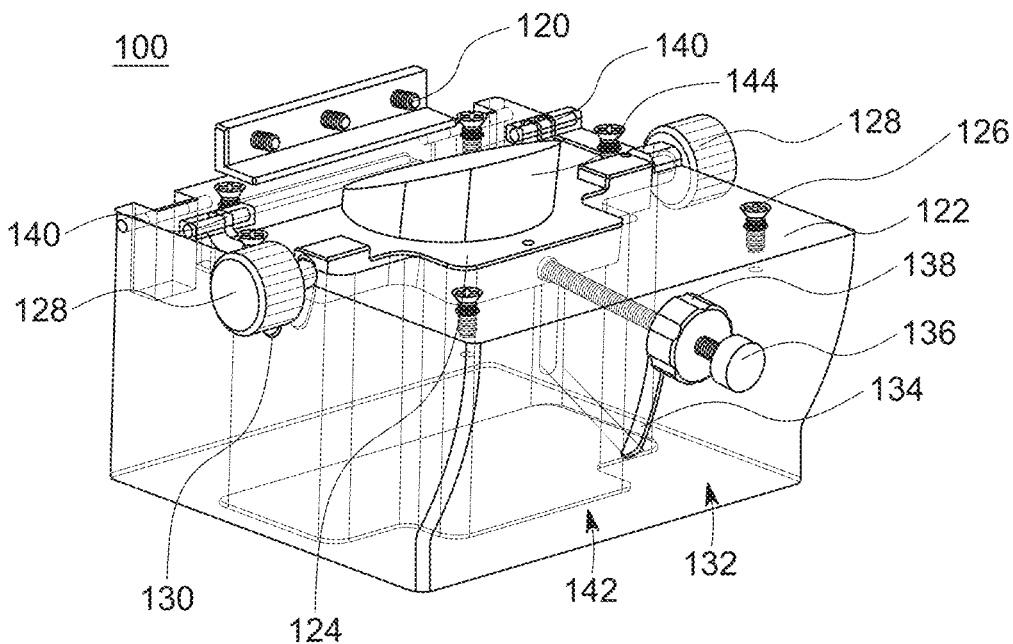
FIG. 38 is a front perspective view of a portion of the orthopedic instrument of FIG. 25 with the housing being shown as transparent, in accordance with the present disclosure.
Figure 39:
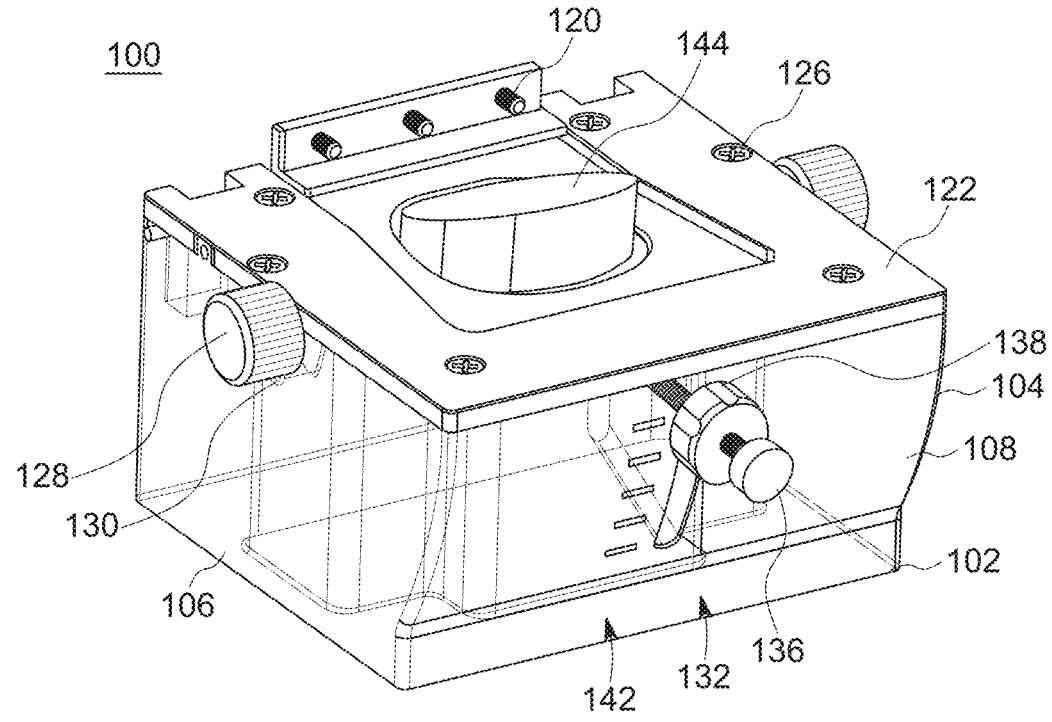
FIG. 39 is an alternate front perspective view of a portion of the orthopedic instrument of FIG. 25 with the housing being shown as transparent, in accordance with the present disclosure.
Figure 40:
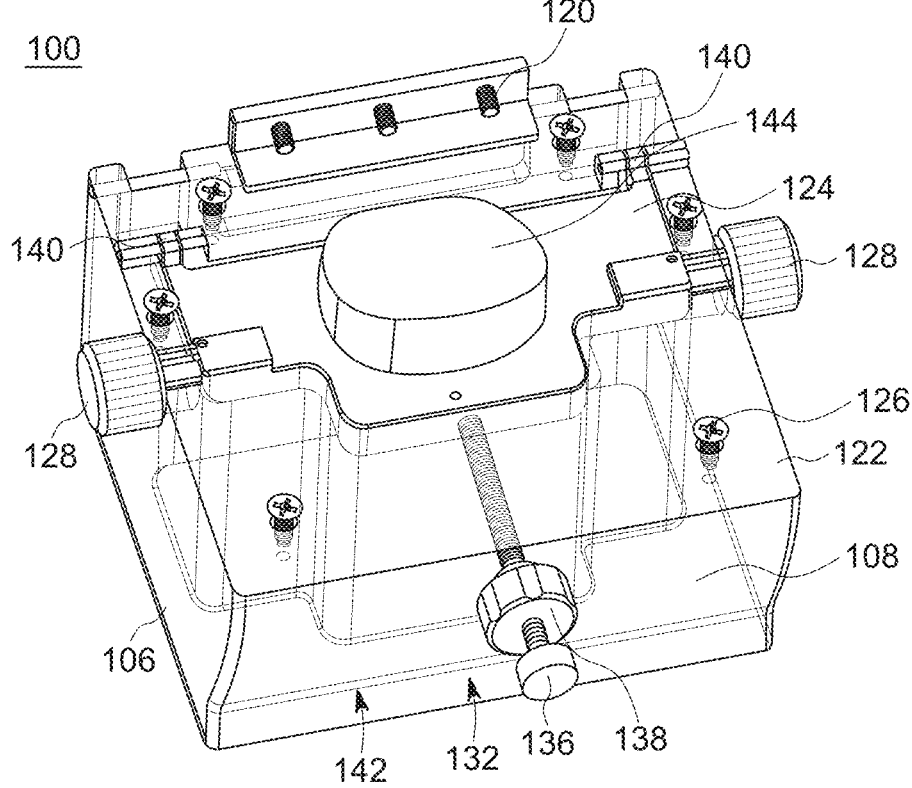
FIG. 40 is a top perspective view of a portion of the orthopedic instrument of FIG. 25 with the housing being shown as transparent, in accordance with the present disclosure.
Figure 41:
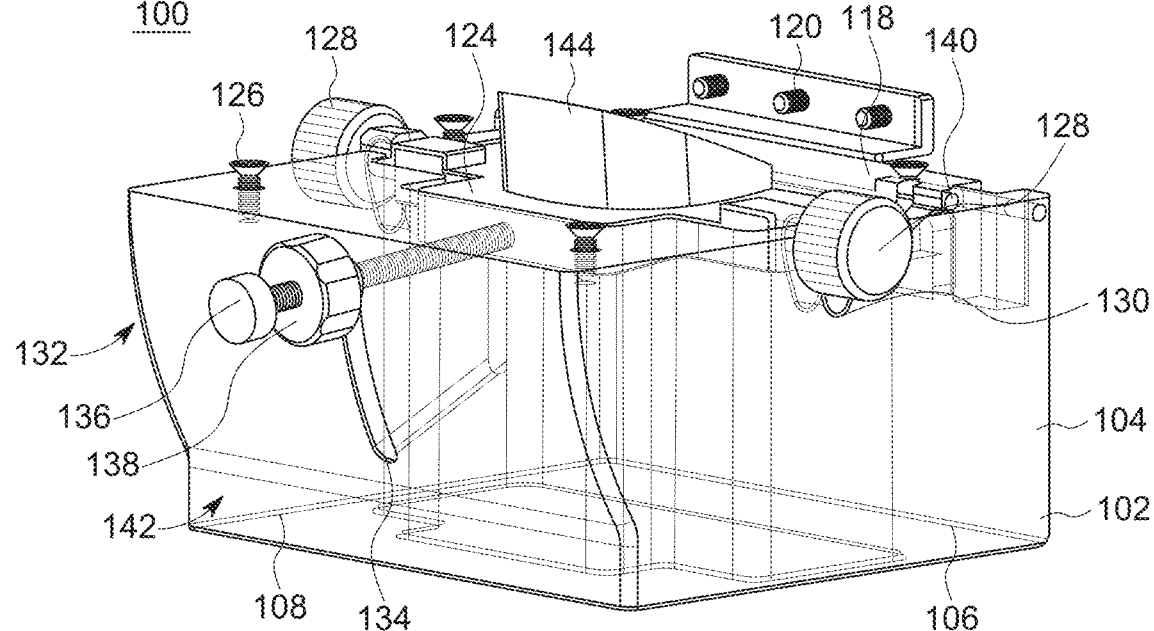
FIG. 41 is an alternate front perspective view of a portion of the orthopedic instrument of FIG. 25 with the housing being shown as transparent, in accordance with the present disclosure.
Figure 42:
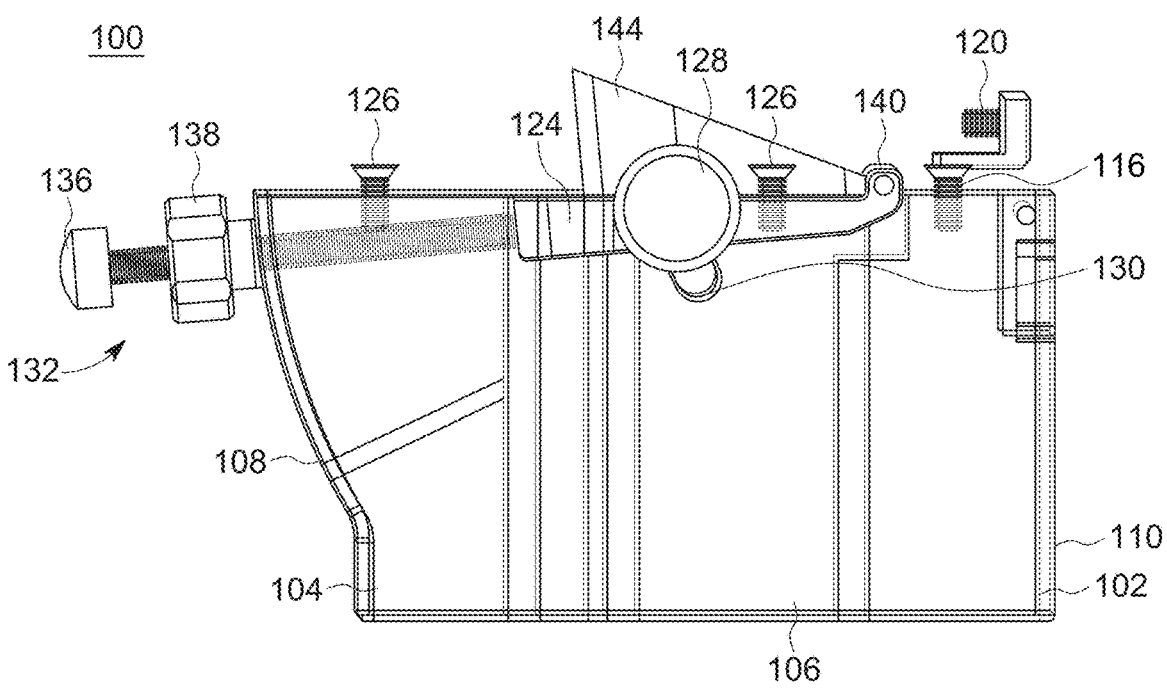
FIG. 42 is a side view of a portion of the orthopedic instrument system of FIG. 25 with the housing being shown as transparent, in accordance with the present disclosure.
Figure 43:
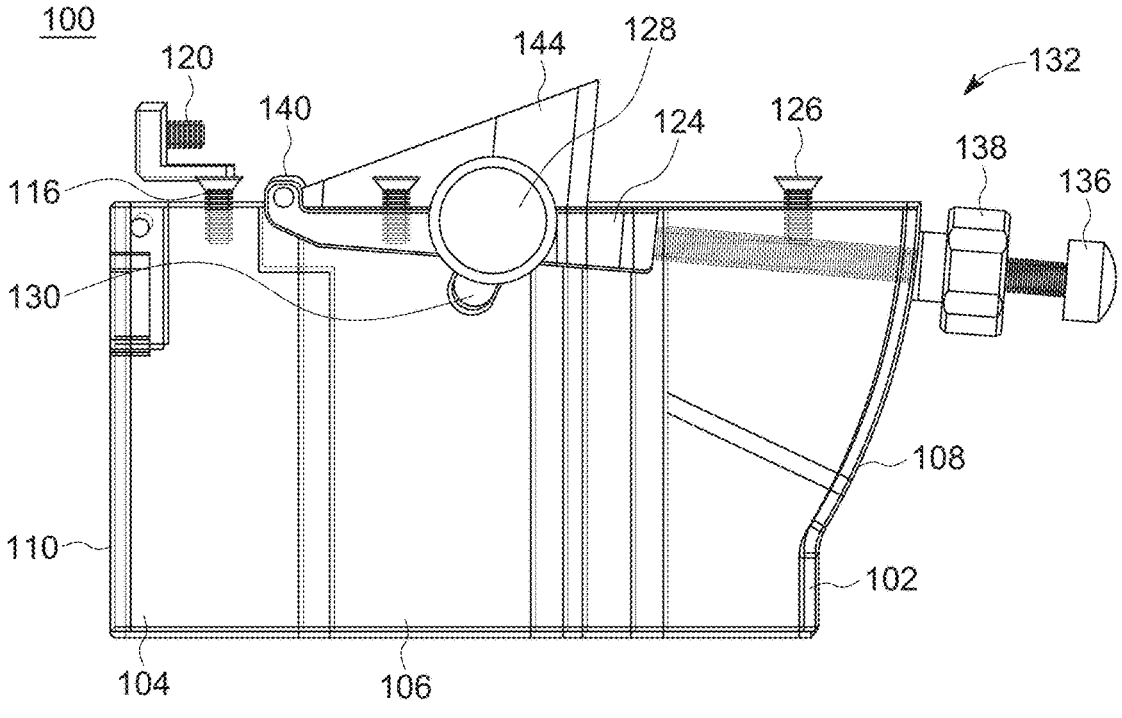
FIG. 43 is an alternate side view of a portion of the orthopedic instrument of FIG. 25 with the housing being shown as transparent, in accordance with the present disclosure.
Figure 44:
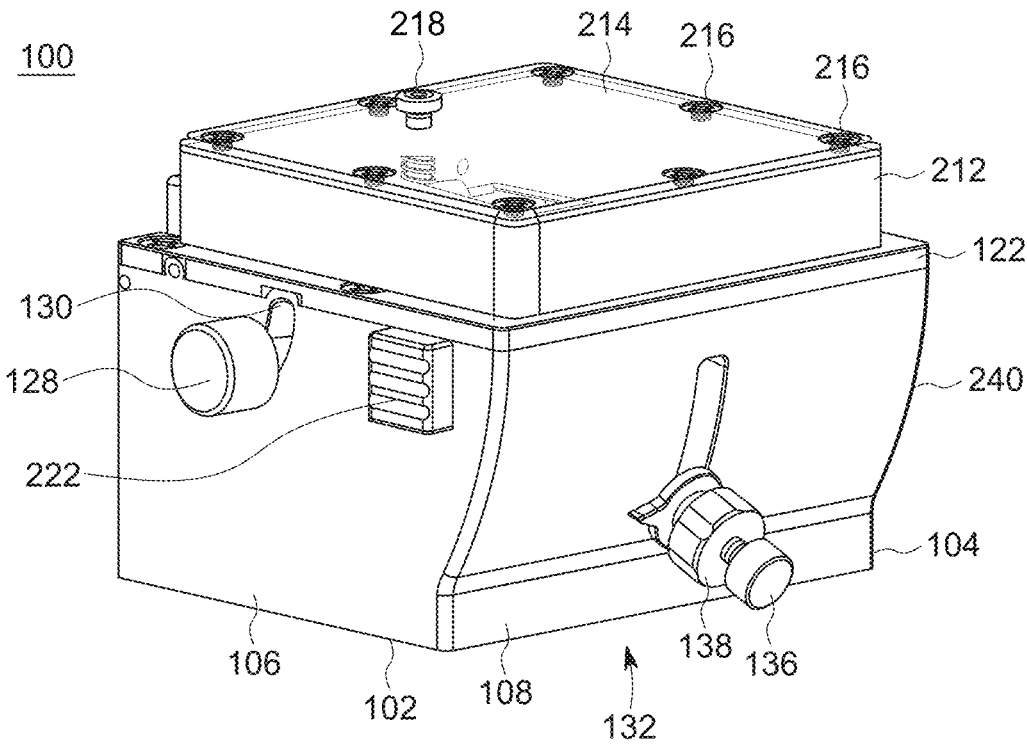
FIG. 44 is a perspective view of an orthopedic instrument, in accordance with the present disclosure.
Figure 45:
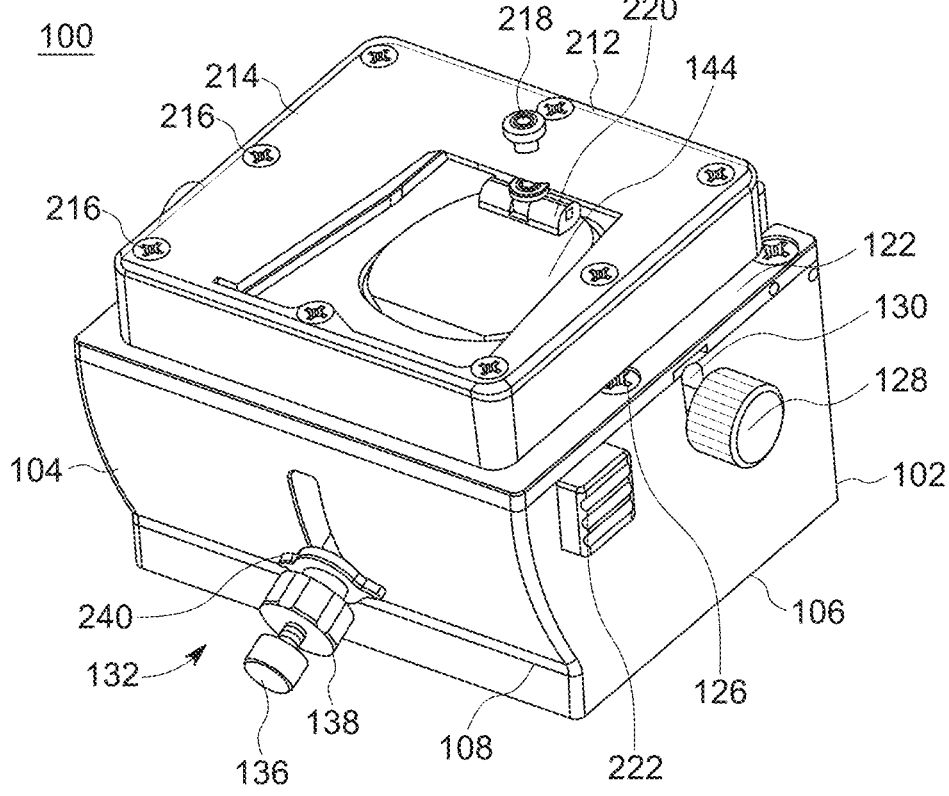
FIG. 45 is top perspective view of the orthopedic instrument of FIG. 44, in accordance with the present disclosure.

A portion of the lid disposed between the hinged couplings between the lid 112 and the hinges 114, in conjunction with a portion of the top surface of the plate 122 adjacent the back side 110 of the housing 104, defines an opening 116 (see FIG. 34). Further, the opening 116 may be positioned substantially below the fasteners 120. As shown in FIGS. 25-47, and more specifically in FIG. 34, the opening 116 is a substantially rectangular-shaped and elongated opening, although the opening 116 may have various alternate geometries, shapes, sizes, and locations relative to the instrument 100 and components thereof in alternate embodiments. The opening 116 (e.g., a slot, etc.) is shown to be configured to receive at least a portion of an instrument therein, for example a distal end of a cutting instrument (not shown) common to surgical procedures including but not limited to a sagittal or reciprocating saw (which may or may not be included in a system/kit with the instrument 100 and/or a biologic implant). In some aspects, the opening 116 may be obstructed by at least a portion of the top surface of the lid 112 when the lid 112 is in an "open" position, but is configured to accept at least a portion of the cutting instrument when in a "closed" position.

The instrument 100 is further shown to include a platform 124 disposed within and releasably coupled with at least a portion of the housing 104. Further, the platform 124 is positioned substantially below the plate 122. As shown in at least FIG. 38, the platform is hingedly (and, in some aspects, releasably) coupled with the housing 104 (which may include at least one of the plate 122 and/or the back side 110 of the housing 104) via a pair of hinges 140. The hinged coupling between the platform 124 and the hinges 140 may be configured to permit movement of the platform 124 in a pivoting fashion about a longitudinal axis extending through each of the hinges 140 (in a fashion similar to that previously described with reference to the lid 112).

The lateral sides 106 of the housing 104 are shown to include a pair of slots 130, with a single slot 130 disposed on each of the lateral sides 106 and positioned substantially opposite one another. As shown, the slots 130 have a substantially upright, curved geometry but may have alternate geometries in some embodiments. Further, the instrument 100 is shown to include a pair of actuators 128 releasably coupled with the platform 124 on a lateral portion thereof and extending laterally from the platform 124 through the slots 130 to a point disposed on the exterior of the housing 104. Each of the actuators 128 is shown to include a knob portion disposed laterally relative to the lateral sides 106, and a shaft portion extending toward the platform 124 where the shaft portion is received within an opening of the platform 124. The platform 124 is shown to include a depression on a central area thereof (not shown, but disposed beneath a biologic implant 144 referred to herein after as "implant 144" which may include a bone wedge or other biologic/graft implant of various sizes, shapes, and geometries) configured to at least partially retain at least a portion of the implant 144. The shaft portion of each of the actuators 128 may extend through the opening of the platform 124 (each actuator 128, on each side of the platform 124) such that the actuator 128 protrudes into the volume of the depression of the platform 124. The actuators 128 may include a narrowed tip (e.g., pointed to facilitate retention) on an end opposite the knob, where the tip is configured to contact a portion of the implant 144 when disposed within the depression. Accordingly, a user may manipulate the actuators 128 in a synchronized fashion or independently such that the tip of the actuators contacts the implant 144 and retains the implant 144 within the depression of the platform 124 (which may include a friction-based retention and/or retention as a result of a small depression formed on/in the implant 144 from the tip of the actuators 128). When the tip of the actuator 128 is in a desired position relative to the platform 124 and the implant 144, the user may than manipulate (e.g., rotate, actuate, etc.) the knob portion of the actuators 128 so as to "lock" the actuators in a desired position and facilitate continued retention of the implant 144. When the actuators 128 are in contact and thus retaining the implant 144 within the depression of the platform 124 (or, when the shaft portion of the actuators are disposed within the openings of the platform 124), any range of motion of the platform 124 may be constrained by a mechanical stop existing between the actuators 128 and the upper/lower limits of the slots 130. It should be noted that the contact points between the tip of the actuators 128 and the implant 144 may be positioned below the top surface of the platform 124 and/or the plate 122 such that any insertion of a cutting instrument within the opening 116 would not contact the actuators 128 (due to the physical barrier(s) of the plate 122 and/or the platform 124).

The front side 108 of the housing 104 is configured to include a slot 134 which, as shown in FIGS. 25-26, 32-33, 38-39, and 41, has a substantially upright geometry (but may have alternate geometries in some embodiments. Further, the instrument 100 is shown to include an adjustment mechanism 132 including a threaded member 136 and a locking member 138 where the locking member 138 is configured to extend from a lateral portion of the front portion of the platform 124 (e.g., opposite the platform from the hinges 140) (either through a coupled connection or integral configuration). The threaded member 136 is shown to extend from the platform 124 toward the slot 134 in the front side 108 and through the slot 134 such that the end of the threaded member 136 opposite the platform 124 is positioned outside the housing 104. Further, as shown and described herein the end of the threaded member 136 opposite the platform 124 includes a knob portion configured to facilitate manipulation of the adjustment mechanism 132 including the threaded member 136 as well as the platform 124 (via the coupled or integral connection) about the pivoting range of motion described previously with reference to the hinges 140. In some aspects, the knob portion of the threaded member 136 may be releasably couplable with the threaded member 136.

The locking member 138 is shown to include a geometry that is the same as and/or similar to a washer or nut, where the threaded member 136 is received through a central opening of the locking member 138 and the locking member 138 is positioned external the housing 104 but adjacent to the front side 108 thereof. In some aspects, the locking member 138 is configured to receive the end of the threaded member 136 opposite the platform 124 after the knob portion has been decoupled, with the knob portion recoupled after the threaded member 136 has been received within the opening of the locking member 138. The knob portion may be configured to have a larger lateral geometry than that of the opening of the locking member 138 so as to promote the retention of the locking member 138 between the front side 108 and the knob portion.

The front side is shown to include a set of markings 142 positioned adjacent to the slot 134. As shown, the markings 142 include numerical markings increasing at consistent intervals moving downward from the top of the slot 134 toward the bottom. In some aspects, the markings may include indications of distance measurements (e.g., mm, inches, etc.) or angulation measurements (e.g., degrees, etc.) and may increase/decrease when moving top to bottom or bottom to top along the slot 134. Accordingly, the adjustment mechanism 132 is configured such that the threaded member 136 may be manipulated within a range of motion defined by the slot 134 when the locking member 138 is not in contact with the front side 110 (and thus in an "unlocked" position). Such manipulation of the threaded member 136 is configured to drive the aforementioned pivoting of the platform 124, where movement of the threaded member 136 upward or downward within the slot 134 adjusts the amount or thickness of the implant 144 extending above the top surface of the plate 122. When the threaded member 136 is positioned adjacent a desired marking 142, the locking member 138 may be actuated along the threaded member 136 (via a threading on the internal surface of the opening) until a surface of the locking member 138 contacts the outer surface 110 thus retaining the threaded member 136 in the desired position adjacent the desired marking 142. In some aspects, the adjustment mechanism 132 may be configured as an infinite adjustment mechanism (e.g., the threaded member 136 may be retained in a position between two of the markings 142 by the locking member 138), or as a finite adjustment mechanism (e.g., the adjustment mechanism and/or the housing 104 includes slots or other features permitting the threaded member 136 to only be locked by the locking member 138 adjacent each of the markings 142).

The instrument 100 and components thereof, as well as other components of surgical kits/systems (including but not limited to those shown and described herein) may be implemented by a physician either preoperatively or intraoperatively according to the method described subsequently herein. However, it should be noted that this method is exemplary and in no way limiting. Further, one or more steps of the method may be skipped, repeated, performed in an alternate order to that described, or replaced with various other steps. Additionally, components implemented in performing the method may vary from those shown and described herein including, for example, the implant 144 and the cutting instruments/tools common to surgical procedures. It should be understood that instruments and components described with reference to the following method are exemplary and may vary in some aspects.

In some aspects, a physician may be provided with or obtain the instrument 100, which may be a component of a kit or system, prior to a surgical procedure. Any kit/system may include, in addition to the instrument 100, at least one implant 144 (e.g., a biologic implant) as well as at least one cutting instrument. Either prior to or during the course of the procedure, the physician may determine a desired size of the at least one implant 144. If done preoperatively, various medical imaging may be incorporated into this determination. Or, if done intraoperatively, various implant sizing trials (which may be included in a system/kit with the instrument 100 and at least one implant 144) may be placed and removed within a void of the patient until a desired size of the at least one implant 144 is determined based on the fit of the sizing trials. Any desired size of the at least one implant 144 may correspond to one or more of a height measurement, an angulation measurement, or other measurements which may correspond to the markings 142 on the instrument 100. The physician may then place the at least one implant 144, one implant 144 at a time, within the depression of the platform 124 and adjust the actuators 128 so the implant 144 is retained in the desired position within the depression of the platform 124. The physician may then manipulate the locking member 138 to an "unlocked" position, and manipulate the threaded member 136 such that it is positioned adjacent to one of the markings 142 that corresponds to the desired size, angulation, and/or other implant parameters. The physician may then manipulate the locking member 138 to a "locked" position so as to retain the threaded member 136 (and thus, the implant 144 and the platform 124) in the desired position. The physician may then close the lid 112 of the instrument 100 so as to expose the opening 116. The physician may then insert a cutting instrument within the slot 116 and manipulate the instrument along the length of the slot 116 so as to cut the implant 144 along a plane parallel to and positioned just above the top surface of the plate. With the lid 112 in a closed position, any debris from the cut is retained within the instrument 100. The physician may then open the lid 112 and, upon ensuring the cut to the implant 144 is complete, adjust the actuators 128 such that the implant 144 may be removed from the instrument 100. The physician may then check to confirm that the size (and/or geometry, and/or shape, etc.) of the implant 144 corresponds to the desired size/shape/angulation/etc. prior to implanting the implant 144 within a patient. In some aspects, the aforementioned method may be repeated if the implant 144 is not of the desired dimensional or angular parameters, or if the physician's desired parameters change, or if a second implant 144 is required for a procedure.

Referring now to FIGS. 44-47, the instrument 100 is shown with select alternate components from those shown and described with reference to FIGS. 25-43, according to an exemplary embodiment. The instrument 100 as shown in FIGS. 44-47 is shown to include a lid 212 that differs from the lid 112 shown in FIGS. 25-43, where the lid 212 is compatible with the instrument 100 as well as various components and associated methods thereof. The lid 212 is shown to include an open central portion which is covered by a window 214 releasably coupled with the lid 212 by fasteners 216 positioned variously about the lid 212 and extending through the window 214 into the lid 212. The window 214 as shown is a solid, transparent component configured to cover the implant 144 when positioned on the platform 124. The lid 212 is further shown to include a button 218 extending from a bottom surface of the window 214 through to the top surface thereof. The button 218 is further shown to include an engagement element 220 coupled with the button 218 and positioned opposite the window 214 from the button 218, as well as a resilient member disposed therebetween. As shown, the resilient member is a spring, but in some aspects the resilient member may include other common resilient elements. Upon actuation (e.g., pressing, pushing, etc.) of the button 218 above the top surface of the window 214, the engagement element is biased downward toward the implant 144 so as to contact the implant 144 and retain the implant 144 in a desired position while a cutting instrument is inserted through the opening 116 and manipulated to reshape the implant 144.

Figures 46, 47:
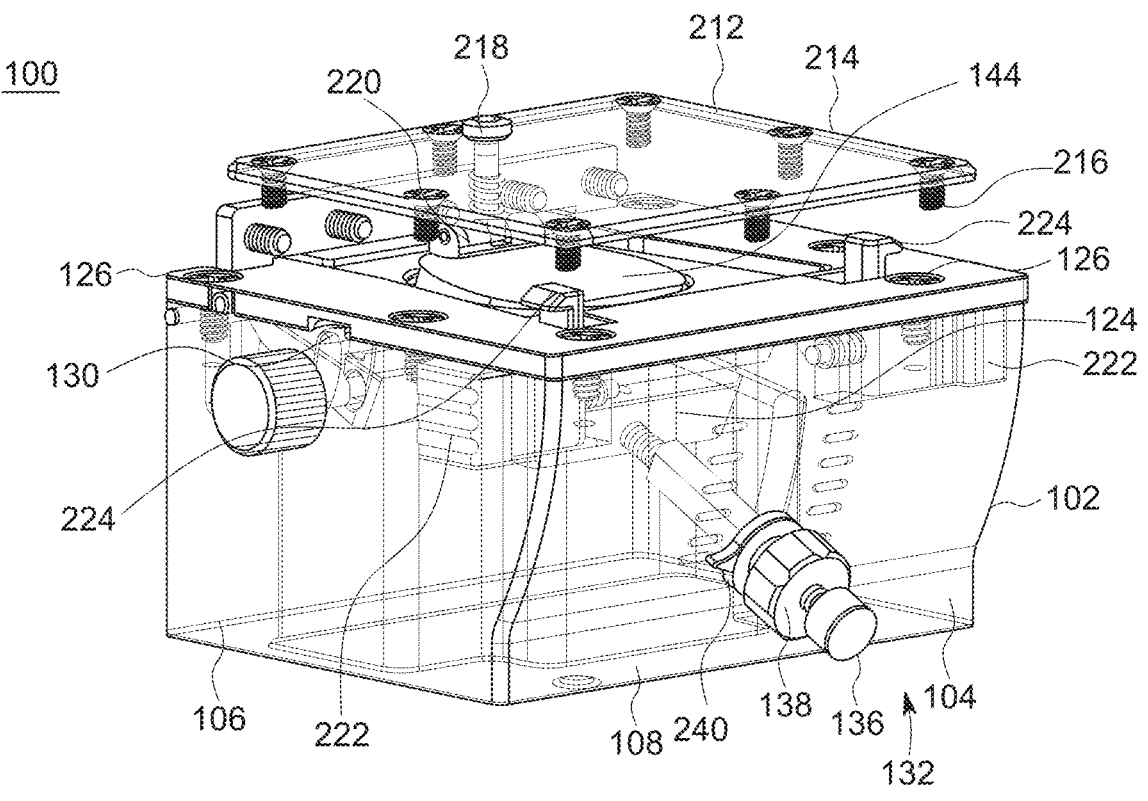
FIG. 46 is a side view of the orthopedic instrument of FIG. 44 with the housing and lid being shown as transparent, in accordance with the present disclosure.
FIG. 47 is a rear perspective view of the orthopedic instrument of FIG. 44, in accordance with the present disclosure.

The instrument 100 as shown in FIGS. 44-47 further includes alternate components configured to engage with the housing 104 and/or other components of the instrument 100, for example the lid 212. The housing 104 is shown to include a pair of actuators 222 disposed in the upper portion of the lateral sides 106 of the housing 104, with the actuators positioned adjacent the front surface 108 of the housing 104. The actuators 222, as shown in FIG. 46, extend into the housing 104 and upward through openings in the plate 122 such that a portion of the actuators 222 are positioned above the plate 122 and adjacent portions of the lid 212. The actuators 222 are shown to include a substantially curved or hooked geometry at an upper portion thereof configured to engage with a portion of the lid 212 so as to retain the lid 212 in a closed position. Further, upon actuation (e.g., pushing, pressing, etc.) of the actuators 222, the curved/hooked upper portion thereof disengages with the lid 212 and thus allows a user to open the lid 212.

Additionally, the threaded member 136 is shown to include an indicator 240 positioned concentrically about the threaded member 136. As shown, the indicator 240 is substantially washer-shaped with an open, circular, central portion through which a length of the threaded member 136 may be received and positioned as shown in FIGS. 44-47. Accordingly, upon actuation of the threaded member 136, the indicator 240 is positioned adjacent one or more markings 142 on the housing 104 thus indicating which height or degree measurement corresponds to the current position of the threaded member 136. As shown, the indicator 240 may be rotatable about the threaded member 136 such that a pointed portion of the indicator 240 may be manipulated from the left side of the slot 134 to the right side and vice-versa.

In some aspects, one or more of the implants 10, 50, and/or 70 may be provided in a surgical system with the instrument 100 and the implant 144. For example, after a physician performs the aforementioned process to reshape the implant 144 using the instrument 100, the implant 144 may be positioned within a volume in a bone or between bony segments created by an osteotomy cut or other surgical procedure. One of the implants 10, 50, 70 may then be coupled with the bone or bony segments using orthopedic fasteners (e.g., screws) such that a portion of the implant 10, 50, 70 (e.g., the central portion 18, 58, 78) is positioned adjacent the implant 144 and thus retains the implant 10, 50, 70 within the aforementioned volume.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. An orthopedic instrument, comprising:
a body comprising a housing, wherein the body further comprises:
  a platform configured to receive an implant;
  at least one retention mechanism configured to retain the implant at least partially on the platform;
  an adjustment mechanism configured to adjust a height of at least a portion of the platform relative to a top surface of the housing; and a lid hingedly coupled with the housing, wherein the top surface of the housing and the lid define a slot configured to receive at least a portion of a cutting instrument.

2. The orthopedic instrument of claim 1, wherein the implant is a biological graft implant.

3. The orthopedic instrument of claim 2, wherein the implant has a substantially wedge-shaped geometry.

4. The orthopedic instrument of claim 1, wherein the at least one retention mechanism comprises a pair of retention mechanisms configured to contact the implant on opposite sides of the implant.

5. The orthopedic instrument of claim 1, wherein the lid comprises a window coupled with the lid, wherein the window is transparent.

6. The orthopedic instrument of claim 5, further comprising at least one actuator positioned at least partially within the housing, wherein at least a first portion of the at least one actuator extends laterally through an opening in a lateral wall of the housing and at least a second portion of the at least one actuator extends vertically through an opening in the implant.

7. The orthopedic instrument of claim 6, wherein the at least one actuator is a pair of actuators positioned on opposite lateral sides of the housing.

8. The orthopedic instrument of claim 7, wherein each of the actuators is configured to releasably engage the lid so as to retain the lid in a closed position.

9. The orthopedic instrument of claim 8, wherein manipulation of the actuators disengages the actuators from the lid.

10. The orthopedic instrument of claim 9, wherein the lid comprises a button releasably coupled with an engagement element.

11. The orthopedic instrument of claim 10, wherein manipulation of the button biases the engagement element such that the engagement element contacts the implant so as to retain the implant in a desired position.

12. A surgical system, comprising:
an instrument, comprising:
  a body comprising a housing, wherein the body further comprises:
    a platform configured to receive a biologic implant;
    at least one retention mechanism configured to retain the biologic implant at least partially on the platform;
    an adjustment mechanism configured to adjust a height of at least a portion of the platform relative to a top surface of the housing; and
    a lid hingedly coupled with the housing, wherein the top surface of the housing and the lid define a slot configured to receive at least a portion of a cutting instrument;
  a first implant configured to be reshaped within the housing of the instrument; and
  a second implant.

\* \* \* \* \*